(12) United States Patent
Lin et al.

(10) Patent No.: US 12,194,015 B2
(45) Date of Patent: *Jan. 14, 2025

(54) COMPOSITION COMPRISING FERROUS AMINO ACID PARTICLES AND METHOD FOR TREATING OR AMELIORATING PANCREAS-RELATED DISEASE USING THE SAME

(71) Applicant: PROFEAT BIOTECHNOLOGY CO., LTD., Taoyuan (TW)

(72) Inventors: Tsun-Yuan Lin, Taoyuan (TW); Mu-Kuei Chen, Taoyuan (TW); Tsang-Tse Chen, Taoyuan (TW); Hsun-Jin Jan, Taoyuan (TW); Chai-Hui Fu, Taoyuan (TW); Kai-Ting Wang, Taoyuan (TW)

(73) Assignee: PROFEAT BIOTECHNOLOGY CO., LTD., Taoyuan (TW)

( * ) Notice: Subject to any disclaimer, the term of this patent is extended or adjusted under 35 U.S.C. 154(b) by 756 days.

This patent is subject to a terminal disclaimer.

(21) Appl. No.: 16/965,181

(22) PCT Filed: Dec. 20, 2018

(86) PCT No.: PCT/CN2018/122406
§ 371 (c)(1),
(2) Date: Jul. 12, 2021

(87) PCT Pub. No.: WO2020/124495
PCT Pub. Date: Jun. 25, 2020

(65) Prior Publication Data
US 2022/0031651 A1 Feb. 3, 2022

(51) Int. Cl.
| A61K 31/295 | (2006.01) |
| A61K 31/7068 | (2006.01) |
| A61P 1/18 | (2006.01) |
| A61P 29/00 | (2006.01) |
| A61P 35/00 | (2006.01) |
| A61P 35/04 | (2006.01) |

(52) U.S. Cl.
CPC ........ *A61K 31/295* (2013.01); *A61K 31/7068* (2013.01); *A61P 1/18* (2018.01); *A61P 29/00* (2018.01); *A61P 35/00* (2018.01); *A61P 35/04* (2018.01)

(58) Field of Classification Search
CPC ................................... A61P 1/18; A61P 35/00
See application file for complete search history.

(56) References Cited

U.S. PATENT DOCUMENTS

| 2015/0065569 | A1* | 3/2015 | Lin | ............... | A61K 31/295 514/502 |
| 2019/0274967 | A1 | 9/2019 | Lin | | |
| 2019/0314322 | A1 | 10/2019 | Lin | | |
| 2019/0358168 | A1 | 11/2019 | Lin | | |
| 2020/0138726 | A1 | 5/2020 | Lin | | |

FOREIGN PATENT DOCUMENTS

| CN | 104955452 B | 6/2017 | |
| CN | 108371668 A | 8/2018 | |
| EP | 3042652 A1 | 7/2016 | |
| JP | 2008525442 A | 7/2008 | |
| JP | 2009523826 A | 6/2009 | |
| JP | 2016510006 A | 4/2016 | |
| JP | 2019519603 A | 7/2019 | |
| JP | 2019536789 A | 12/2019 | |
| WO | WO2002030947 A2 | 4/2002 | |
| WO | WO2017201701 A1 | 11/2017 | |
| WO | WO-2018098804 A1 * | 6/2018 | ........... A61K 31/198 |

OTHER PUBLICATIONS

Hicks, A.M. et al., Pancreas adenocarcinoma: ascites, clinical manifestations, and management implications, Dec. 1, 2016, Clinical Colorectal Cancer, vol. 15, 24 pages. (Year: 2016).*
Heinemann, V. Gemcitabine-based combination treatment of pancreatic cancer, Feb. 2002, Seminars in Oncology, vol. 29, 25-35 (Year: 2002).*
Pineda, O., and Ashmead, H. D., Effectiveness of treatment of iron-deficiency anemia in infants and young children with ferrous bis glycinate chelate, May 2001, Nutrition.
Ribeiro, L. C., and Sigulem, D. M., Treatment of iron deficiency anemia with iron bis-glycinate chelate and growth of young children. 2008. The Revista de Nutrição.
Basf, Safety Data Sheet Iron-Glycinate, Jan. 11, 2019, Internet Web Page.
Weiss, I. M., Muth, C., Drumm, R., and Kirchner, H. O., Thermal decomposition of the amino acids glycine, cysteine, aspartic acid, asparagine, glutamic acid, glutamine, arginine and histidine., 2018, BMC biophysics.
Macmillan Cancer Support, Chemotherapy for pancreatic cancer, Nov. 30, 2015, Internet Web Page.

* cited by examiner

*Primary Examiner* — Craig D Ricci
*Assistant Examiner* — Paul Hoerner
(74) *Attorney, Agent, or Firm* — WPAT, PC

(57) ABSTRACT

The present invention provides a composition, comprising ferrous amino acid chelate particles sintered from ferrous amino acid chelate, wherein the average particle size of the ferrous amino acid chelate particles ranges from 500 nm to 2600 nm, and the average molecular weight of the particles ranges from 1,500 Dalton to 600,000 Dalton. Besides, the present invention can be used for manufacturing a medicament for treating or ameliorating a pancreas-related disease, wherein the medicament comprises an effective amount of the composition and a pharmaceutically acceptable carrier.

5 Claims, 39 Drawing Sheets abnormally swollen gall

COMPOSITION COMPRISING FERROUS AMINO ACID PARTICLES AND METHOD FOR TREATING OR AMELIORATING PANCREAS-RELATED DISEASE USING THE SAME

CROSS REFERENCE

This application is a 35 U.S.C. § 371 national phase application of International Application Serial No. PCT/CN2018/122406, filed Dec. 20, 2018, the entire content of which is incorporated by reference herein.

BACKGROUND OF THE INVENTION

1. Field of the Invention

The present invention relates to a composition comprising ferrous amino acid chelate particles sintered from ferrous amino acid chelate, and relates to use thereof in treating or ameliorating a pancreas-related disease.

2. Description of the Prior Arts

The common pancreas-related diseases include pancreatic cancer and pancreatitis. The difficulties in treating pancreas-related diseases lie in the location and function of the pancreas, and the limited methods of treatment. The development of pancreatic cancer treatments is relatively slow compared to that of other various cancers. So far, the overall five-year survival rate of pancreatic cancer is only 9%. Pancreatic cancer is the fourth leading cause of death. In Taiwan, pancreatic cancer is the eighth leading cause of death and causes 8.5 deaths per 100 thousand people every year. The reasons of the slow development could be the limited applicable medicaments. Therefore, the drug development in pancreatic cancer is highly valuable. Malignant ascites is a common clinical sign in the advanced stage of pancreatic cancer and mainly caused by the peritoneal infiltration of pancreatic cancer. The malignant ascites can be hemorrhagic ascites or serous ascites. As the volume of ascites increases and the organs in abdominal cavity are compressed, the appetite might be decreased. Some patients have slow peristalsis, or paralytic ileus which causes vomiting. The formation of ascites not only affects the life quality of patients but also has adverse effects on the treatment of advanced stage and recovery in patients. Pancreatitis is the phenomenon that the digestive enzymes produced by the pancreas start to digest the pancreas and the surrounding tissues and cause inflammation. There is no corresponding therapeutic medicament, so the supportive care is usually given to help the pancreas heal itself. Therefore, it is necessary to develop a medicament for effectively treating or ameliorating pancreas-related diseases.

SUMMARY OF THE INVENTION

One of the objectives of the present invention is to provide a medicament for effectively treating or ameliorating pancreas-related diseases. To achieve the above purpose, the present invention provides a composition, and said composition can be used for treating or ameliorating pancreas-related diseases. Said composition comprises ferrous amino acid chelate particles sintered from ferrous amino acid chelate. The ferrous amino acid chelate particles have an average particle size ranging from 500 nm to 2600 nm and an average molecular weight ranging from 1,500 Dalton to 600,000 Dalton.

In one embodiment, preferably, said ferrous amino acid chelate particles have an average molecular weight ranging from 1,500 Dalton to 15,000 Dalton. In another embodiment, preferably, said ferrous amino acid chelate particles have an average molecular weight ranging from 400,000 Dalton to 550,000 Dalton. More preferably, said ferrous amino acid chelate particles have an average molecular weight of 550,000 Dalton Preferably, the chelating ratio of ferrous to amino acid of the ferrous amino acid chelate in said composition is between 1:1 and 1:4.

Preferably, the chelating ratio of ferrous to amino acid of the ferrous amino acid chelate in said composition is between 1:1.5 and 1:2.5.

Preferably, the ferrous amino acid chelate in said composition is prepared by mixing inorganic iron and amino acid and heating at 60° C. to 90° C. for 8 hours to 48 hours to obtain the composition comprising ferrous amino acid chelate, wherein the weight ratio of inorganic iron to amino acid is between 1:1.2 and 1:1.5.

More preferably, the inorganic iron is ferrous sulfate, ferrous chloride, ferrous pyrophosphate, or any combination thereof. More preferably, the amino acid is glycine.

According to the present invention, the term "effective amount" refers to a dosage which effectively achieves desired treatment or amelioration of pancreas-related diseases during a required period of time. According to the present invention, it refers to administering a specific amount range of the composition comprising ferrous amino acid chelate particles sintered from ferrous amino acid chelate that can reduce the cell survival rate of human or mouse pancreatic cancer cells, induce pancreatic cancer cell death, inhibit migration and invasion of human pancreatic cancer cells, inhibit the tumor growth of orthotopic xenograft pancreatic cancer, reduce or ameliorate the malignant ascites from the advanced stage of orthotopic xenograft pancreatic cancer, or treat or ameliorate the pancreatitis.

Preferably, said composition of the present invention can be administered to a subject, such as a human, a mouse, a dog, a cat, etc. The effective amount of said composition ranges from 0.1 mg/kg/day to 120 mg/kg/day.

Preferably, the effective amount of said composition for a mouse ranges from 1 milligram per kilogram per day (mg/kg/day) to 120 mg/kg/day. More preferably, it ranges from 10 mg/kg/day to 120 mg/kg/day. More preferably, it ranges from 24 mg/kg/day to 72 mg/kg/day.

Preferably, the effective amount of said composition for a dog or a cat ranges from 0.1 mg/kg/day to 20 mg/kg/day. More preferably, it ranges from 1 mg/kg/day to 5 mg/kg/day.

Preferably, the effective amount of said composition for a human ranges from 1 mg/day to 7000 mg/day. More preferably, it ranges from 10 mg/day to 700 mg/day. The above dosage is calculated in accordance with the guidance document "Estimating the Maximum Safe Starting Dose in Initial Clinical Trials for Therapeutics in Adult Healthy Volunteers" published by the U.S. Food and Drug Administration in 2005.

According to the present invention, the "pharmaceutically acceptable carrier" includes, but is not limited to, reducing agents, solvents, emulsifiers, suspending agents, decomposers, binding agents, excipients, stabilizing agents, chelating agents, diluents, gelling agents, preservatives, lubricants, surfactants and other similar carriers or the carriers that are suitable for the present invention.

Preferably, the "reducing agents" include, but are not limited to, ascorbic acid, citric acid, acetic acid, propionic acid, butyric acid, lactic acid, malic acid, sulfonic acid, succinic acid, or any combination thereof.

In accordance with the present invention, the "medicament" can be prepared in various forms, including, but not limited to, liquid, semi-solid and solid dosage forms, such as liquid solutions, emulsions, suspensions, powder, tablets, pills, lozenges, troches, chewing gum, capsules, liposomes, suppositories, and other similar dosage forms or the dosage forms that are suitable for the present invention.

Preferably, the medicament is in an enteral or parenteral dosage form.

More preferably, said enteral dosage form is an oral dosage form. Said oral dosage form is a solution, an emulsion, a suspension, powder, a tablet, a pill, a lozenge, a troche, chewing gum, or a capsule.

Preferably, said pancreas-related disease includes, but is not limited to, pancreatic cancer, pancreatic cancer metastasis, ascites produced from pancreatic cancer, and pancreatitis.

Preferably, said composition is administered with gemcitabine. More preferably, said gemcitabine is administered with a dosage regimen comprising one or more gemcitabine cycles, and each gemcitabine cycle is composed of administering gemcitabine twice per week for three weeks and discontinuing gemcitabine on the fourth week.

Said composition of the present invention can treat or ameliorate the pancreas-related disease without significant side-effects. It shows better therapeutic effect of treating or ameliorating the orthotopic xenograft pancreatic cancer and with less hepatotoxic side-effects, such as jaundice, when administered with gemcitabine.

DETAILED DESCRIPTION OF THE PREFERRED EMBODIMENTS

Figure 1:
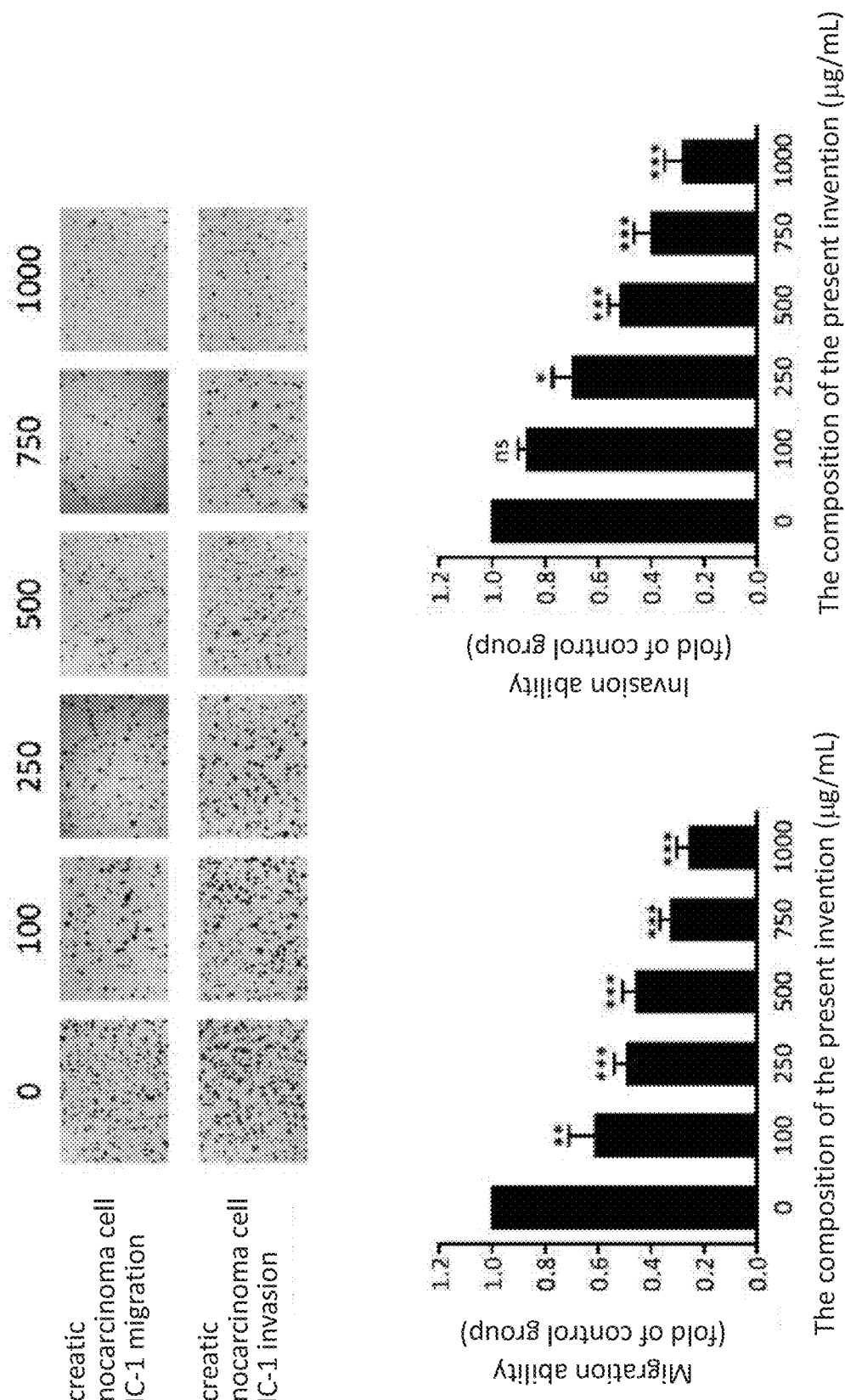
FIG. 1 shows the cell migration ability and invasion ability of PANC-1 cells after treated with the composition of the present invention in a dose-dependent manner for 24 hr, so as to analyze the repression of cell motility by the composition of the present invention in PANC-1 cells. (The error bars indicate the mean±s.d. of at least three independent experiments; ns indicates no significant difference, * indicates $p<0.05$,  indicates $p<0.01$,* indicates $p<0.001$; Student t test)
Figure 2:
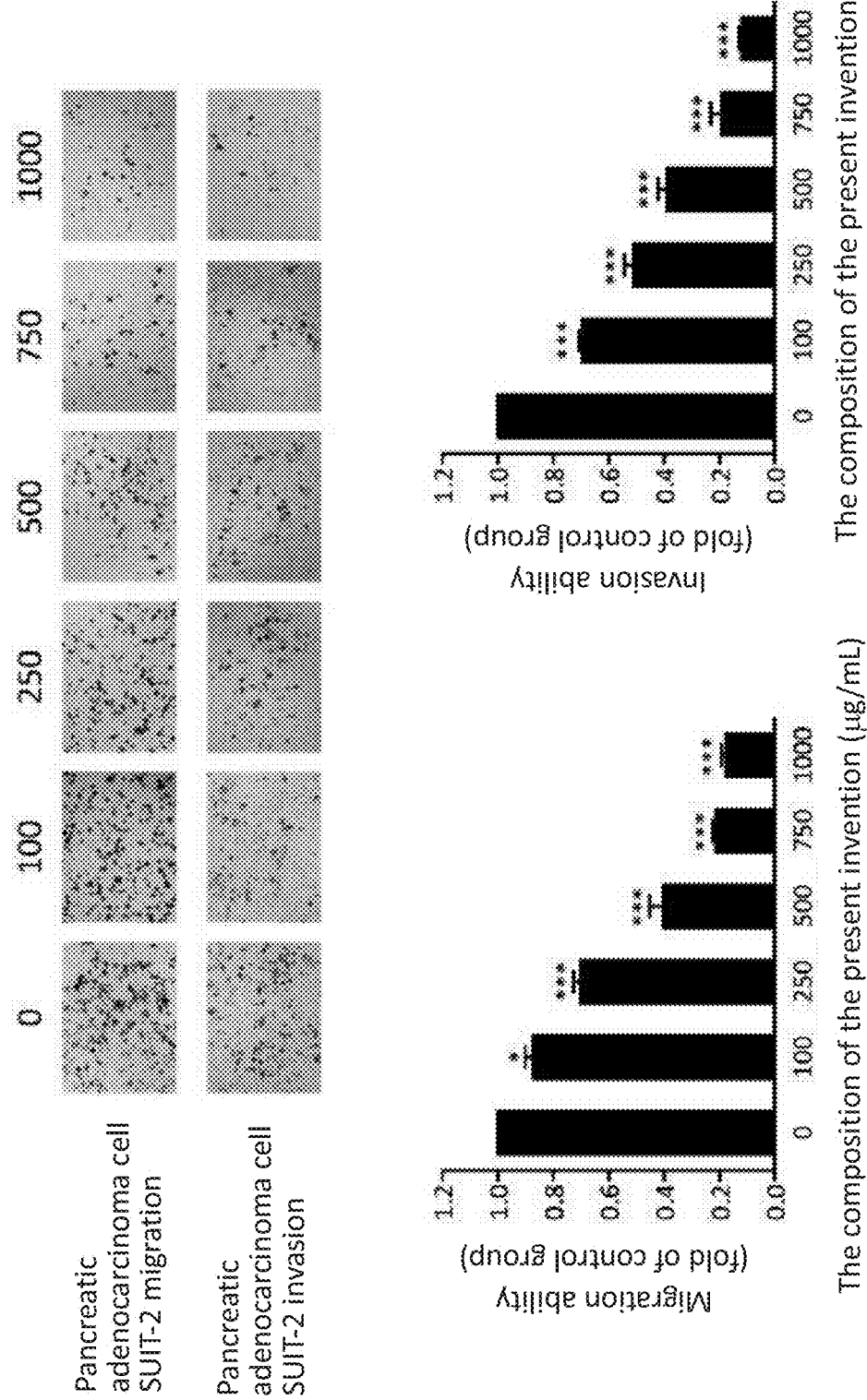
FIG. 2 shows the cell migration ability and invasion ability of SUIT-2 cells after treated with the composition of the present invention in a dose-dependent manner for 24 hr, so as to analyze the repression of cell motility by the composition of the present invention in SUIT-2 cells. (The error bars indicate the mean±s.d. of at least three independent experiments; ns indicates no significant difference,  indicates $p<0.05$, * indicates $p<0.001$; Student t test.)
Figure 3:
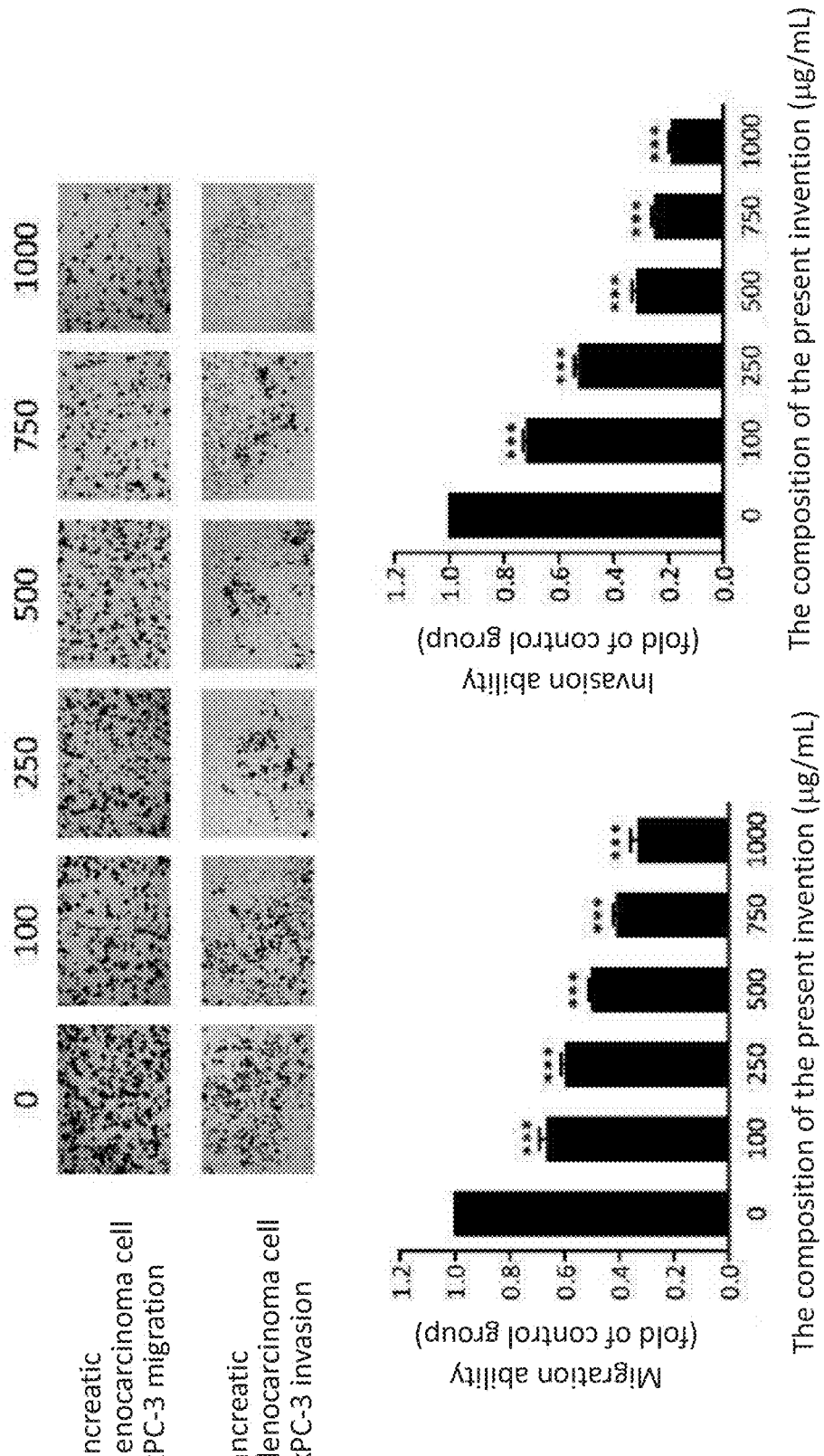
FIG. 3 shows the cell migration ability and invasion ability of BxPC-3 cells after treated with the composition of the present invention in a dose-dependent manner for 24 hr, so as to analyze the repression of cell motility by the composition of the present invention in BxPC-3 cells. (The error bars indicate the mean±s.d. of at least three independent experiments; ns indicates no significant difference, *** indicates $p<0.001$; Student t test.)
Figure 4:
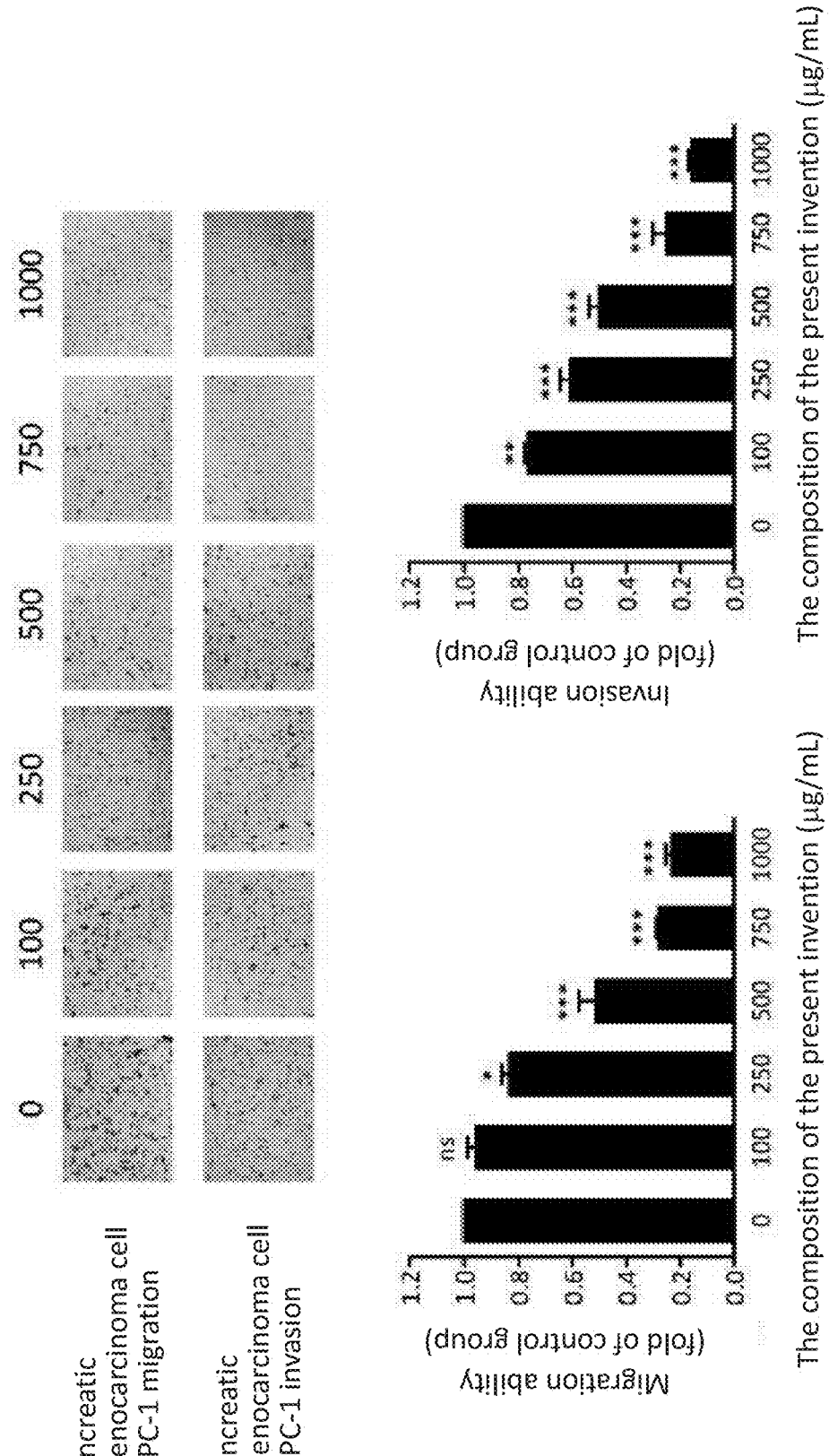
FIG. 4 shows the cell migration ability and invasion ability of AsPC-1 cells after treated with the composition of the present invention in a dose-dependent manner for 24 hr, so as to analyze the repression of cell motility by the composition of the present invention in AsPC-1 cells. (The error bars indicate the mean±s.d. of at least three independent experiments; ns indicates no significant difference, * indicates $p<0.05$,  indicates $p<0.01$,* indicates $p<0.001$; Student t test)
Figure 5A:
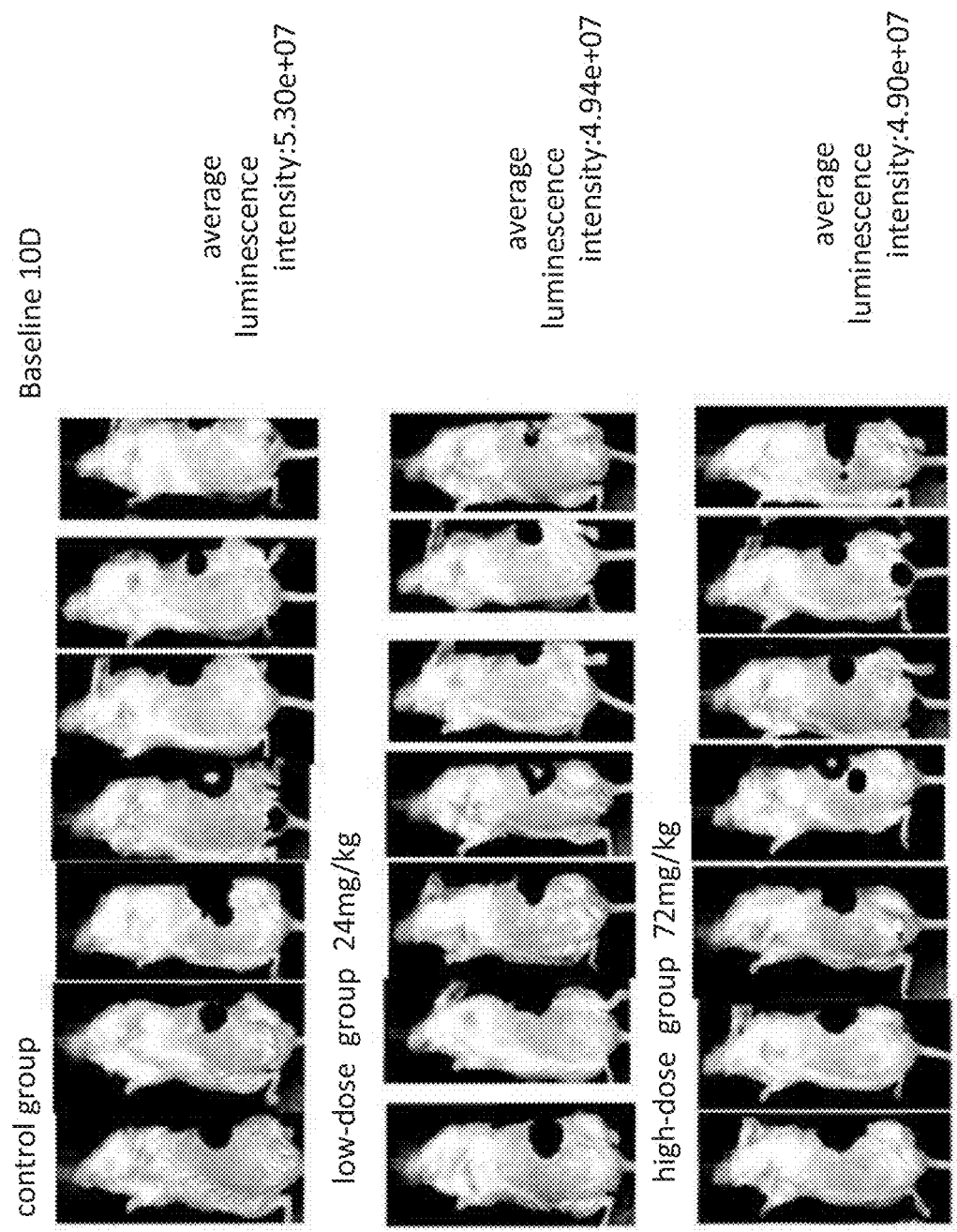
FIG. 5A is the bioluminescence image of orthotopic xenograft pancreatic cancer tumor with the treatment of the composition of the present invention at Baseline 10D.
Figure 5B:
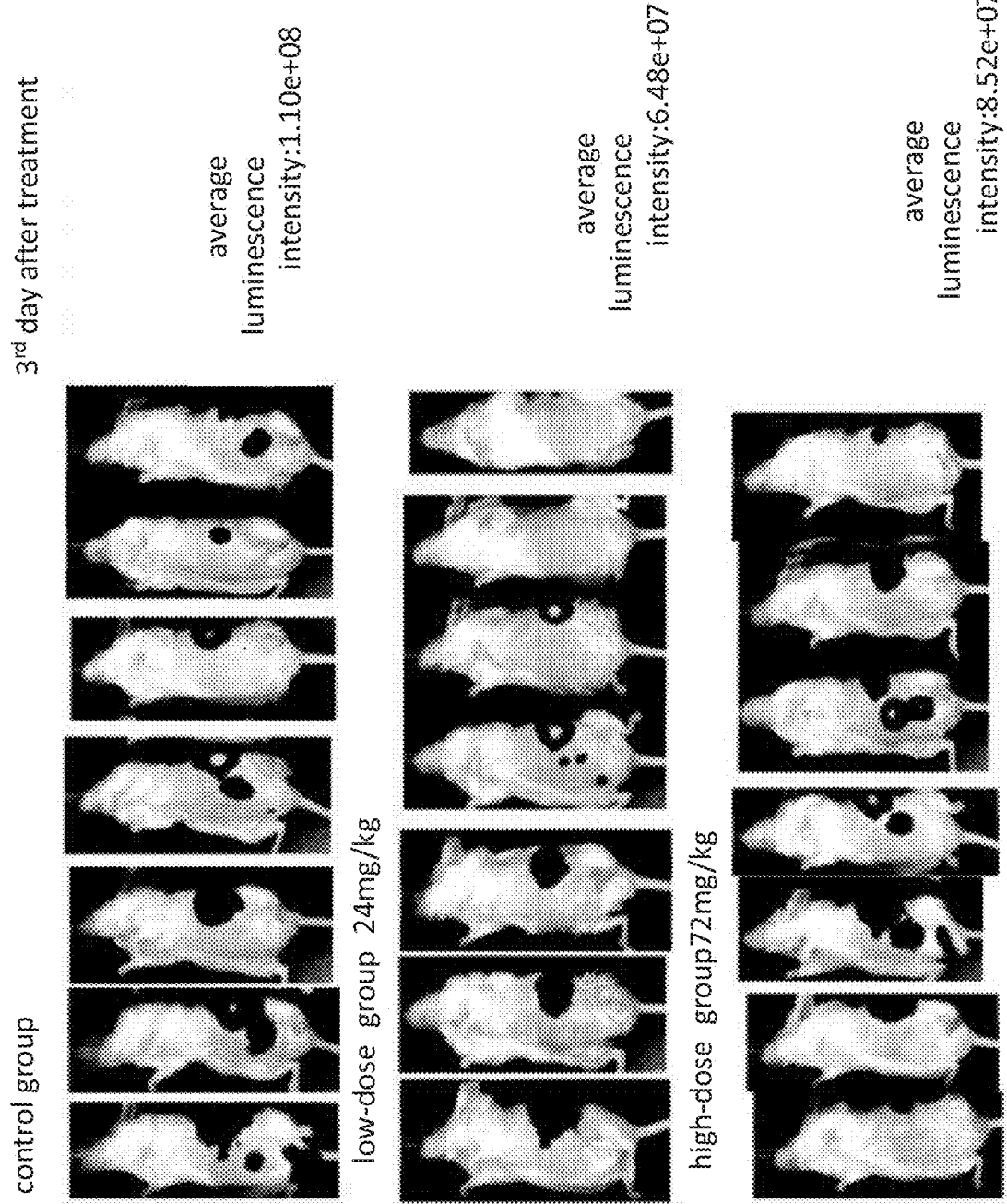
FIG. 5B is the bioluminescence image of orthotopic xenograft pancreatic cancer tumor with the treatment of the composition of the present invention on the $13^{th}$ day of experiment.
Figure 5C:
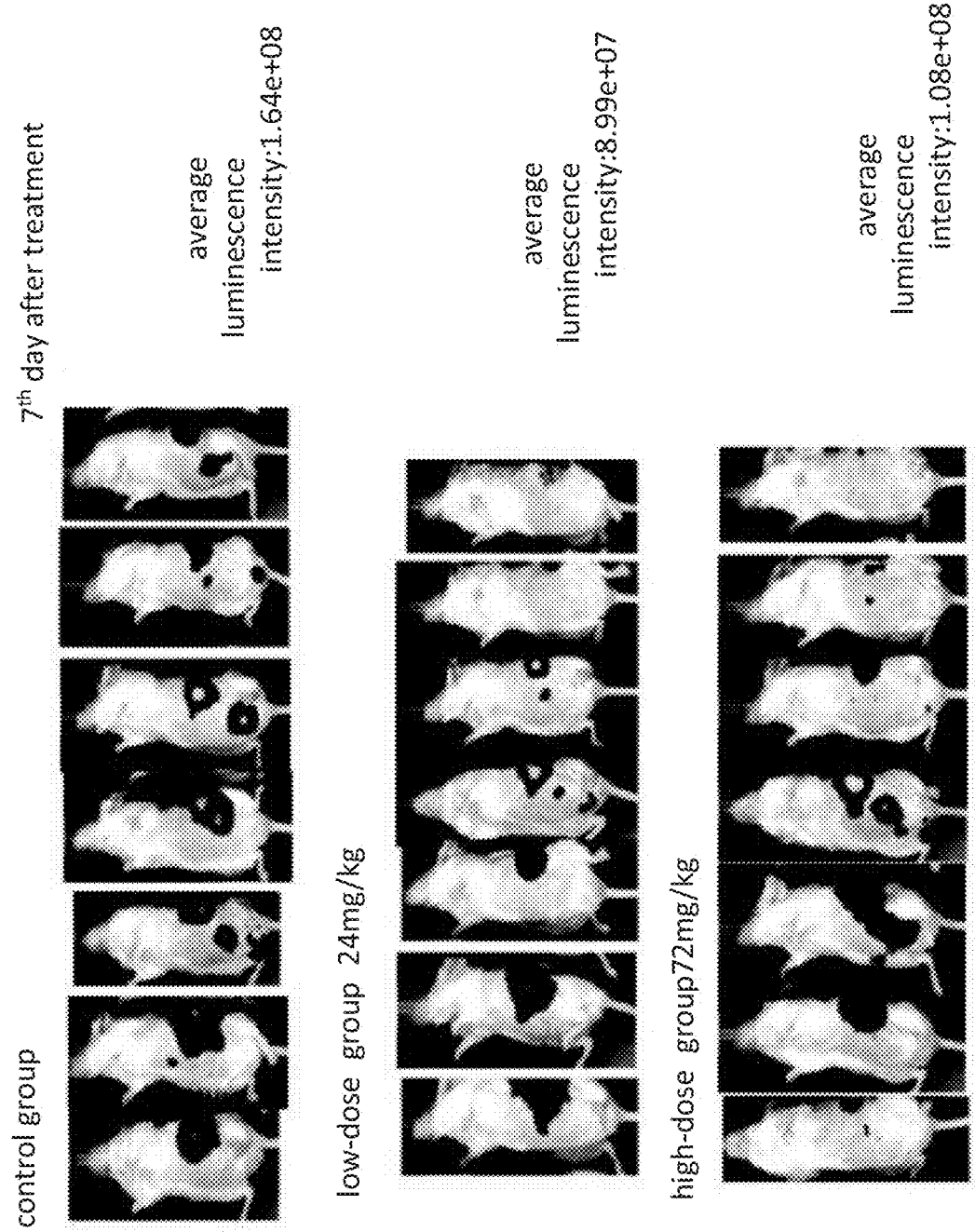
FIG. 5C is the bioluminescence image of orthotopic xenograft pancreatic cancer tumor with the treatment of the composition of the present invention on the $17^{th}$ day of experiment.
Figure 5D:
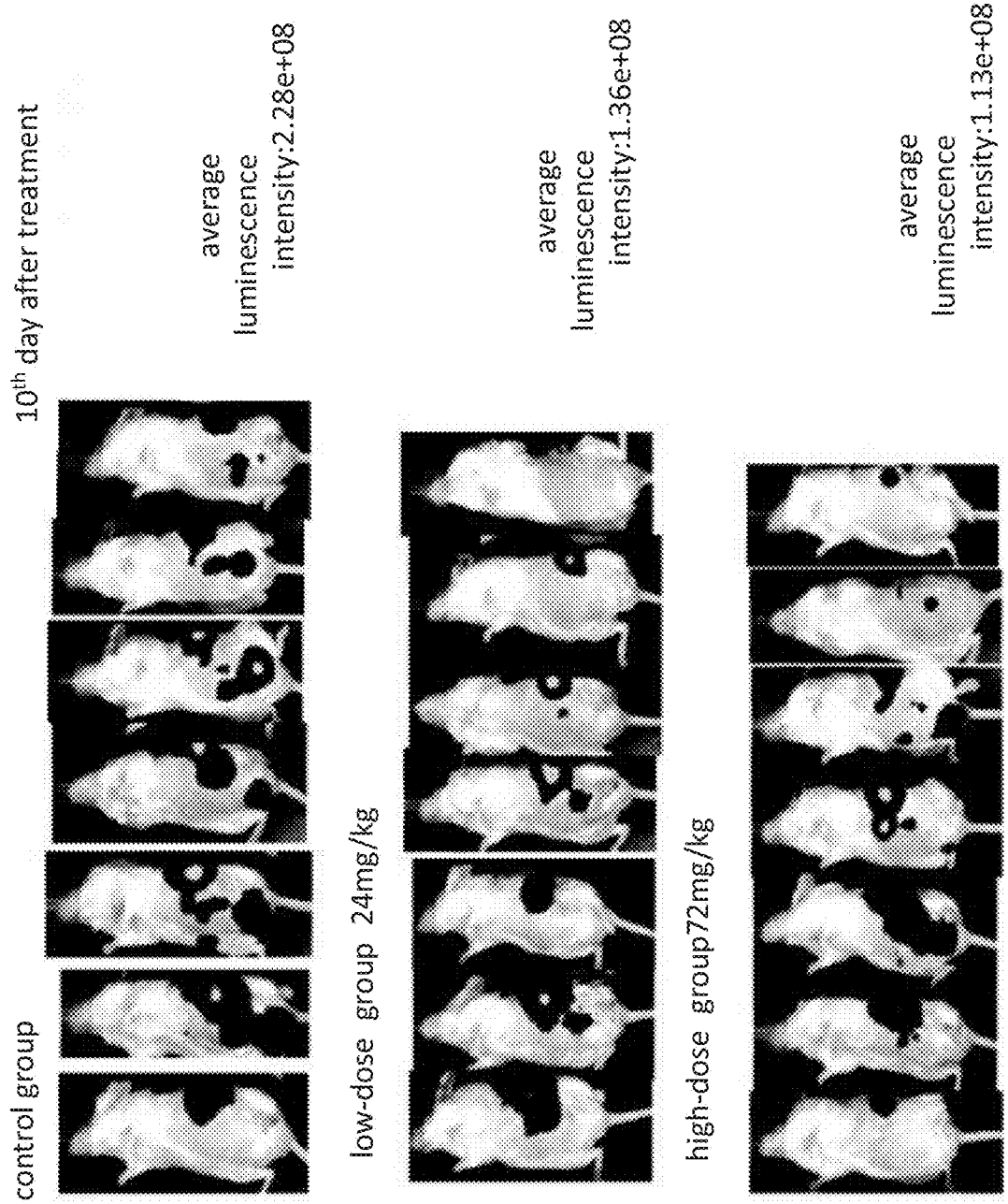
FIG. 5D is the bioluminescence image of orthotopic xenograft pancreatic cancer tumor with the treatment of the composition of the present invention on the $20^{th}$ day of experiment.
Figure 5E:
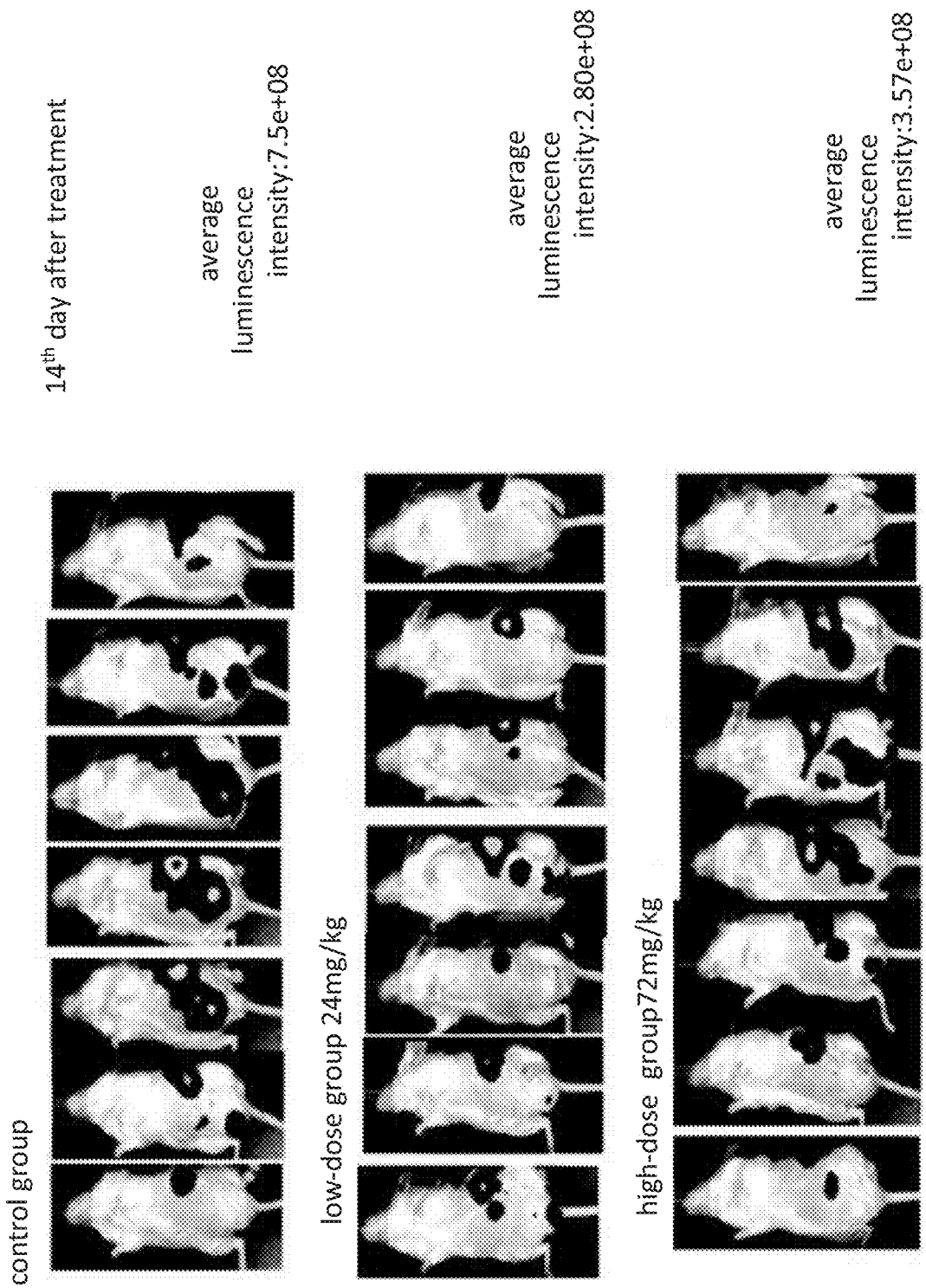
FIG. 5E is the bioluminescence image of orthotopic xenograft pancreatic cancer tumor with the treatment of the composition of the present invention on the $24^{th}$ day of experiment.
Figure 5F:
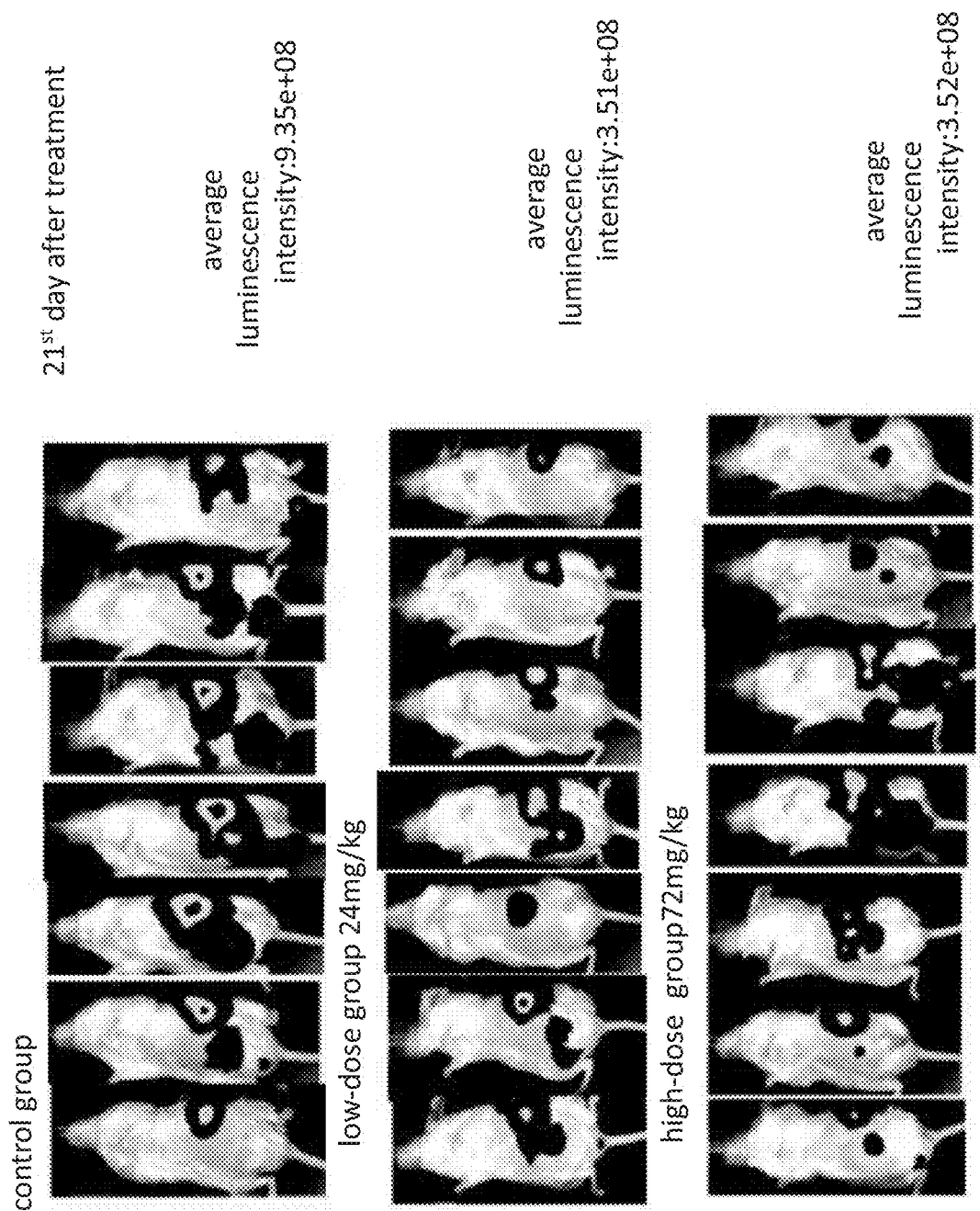
FIG. 5F is the bioluminescence image of orthotopic xenograft pancreatic cancer tumor with the treatment of the composition of the present invention on the $31^{st}$ day of experiment.
Figure 5G:
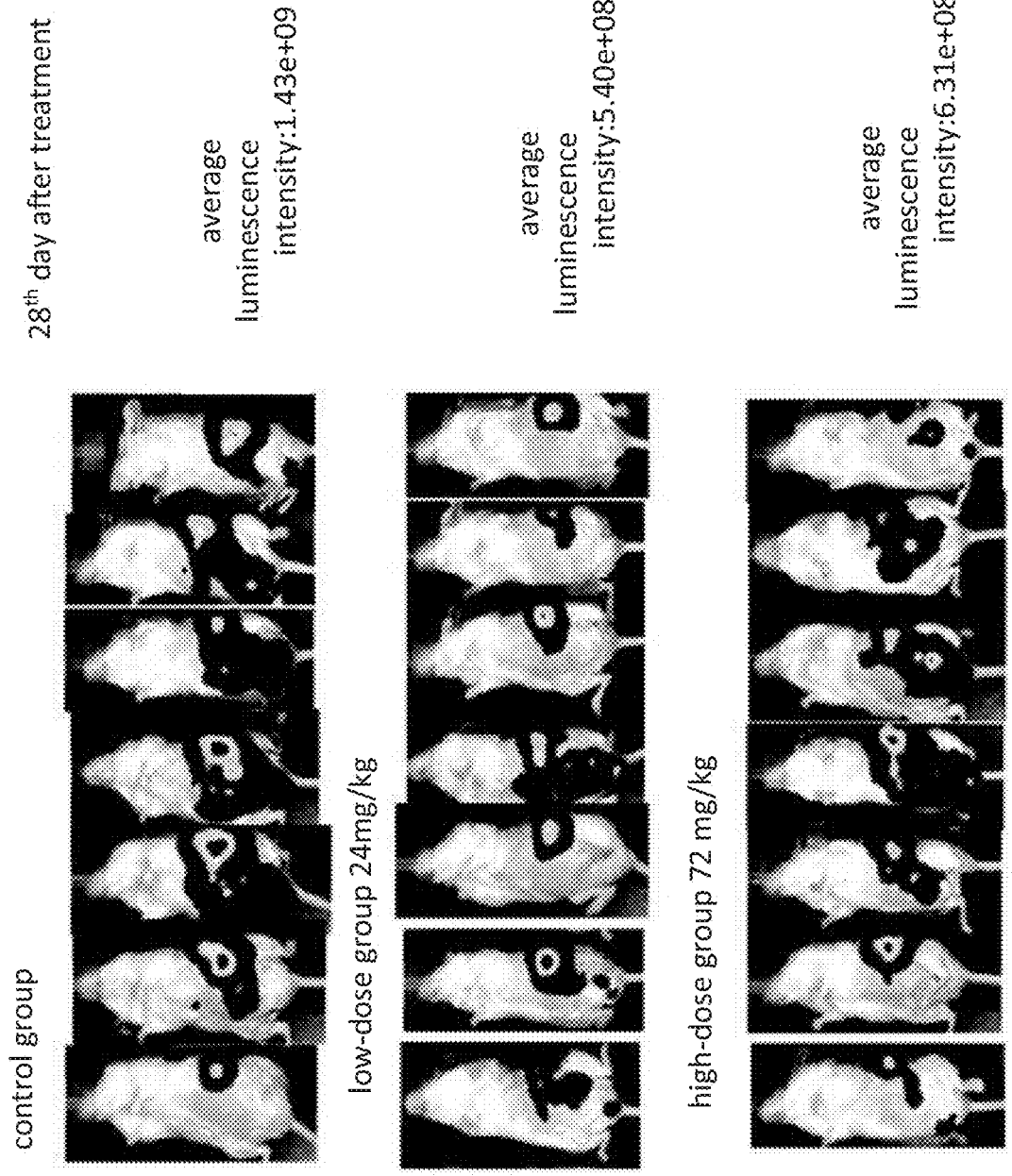
FIG. 5G is the bioluminescence image of orthotopic xenograft pancreatic cancer tumor with the treatment of the composition of the present invention on the $38^{th}$ day of experiment.
Figure 6:
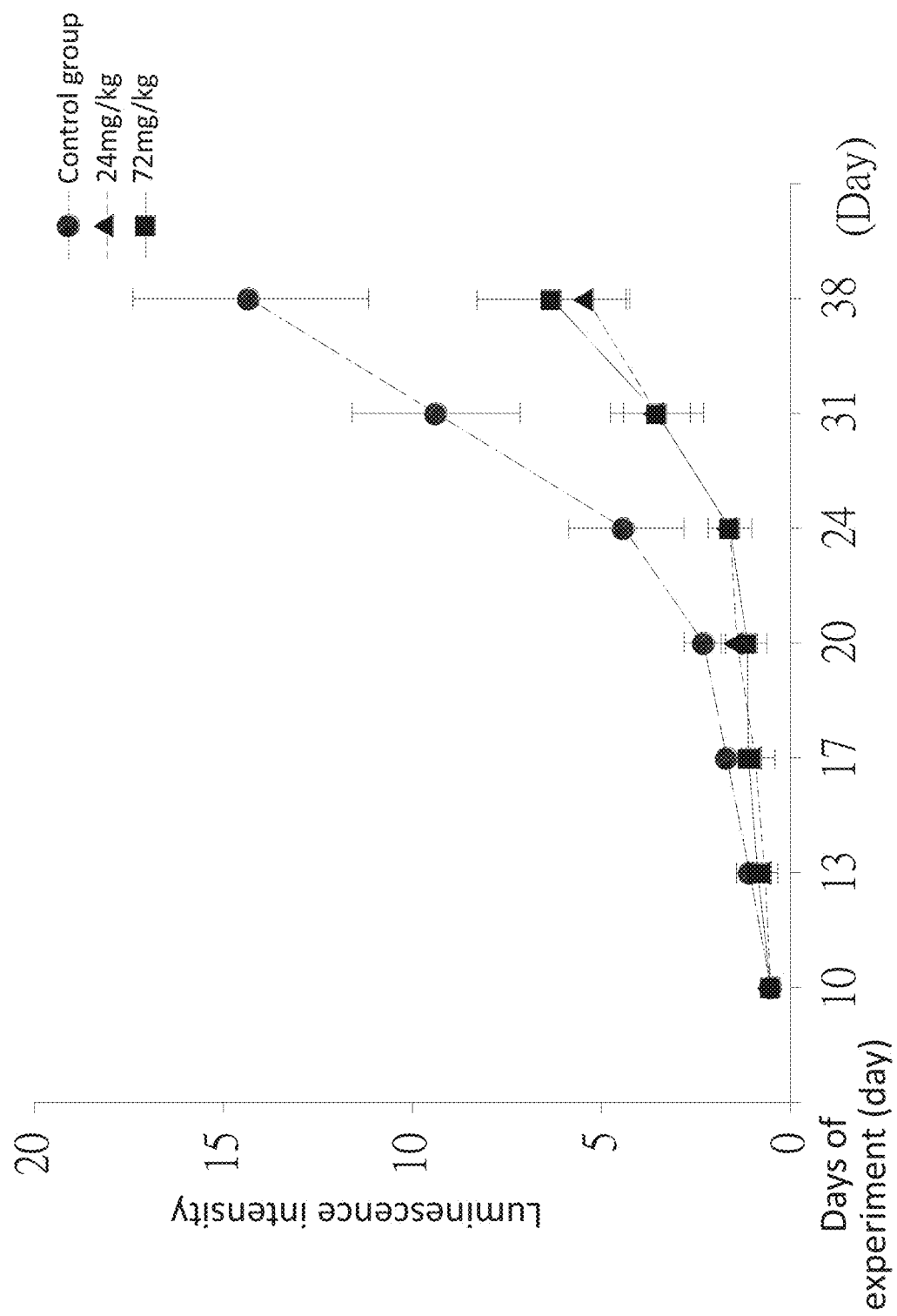
FIG. 6 is the run chart of the tumor growth in orthotopic xenograft pancreatic cancer mice with the treatment of the composition of the present invention.

The present invention is further explained through the following embodiments. The present invention should not be limited to the contents of the embodiments. A person having ordinary skill in the art can do some improvement or modifications which are not departing from the scope of the present invention.

Preparation Example 1: Preparation of the Composition Comprising Ferrous Amino Acid Particles The composition comprising ferrous amino acid chelate particles was prepared by Taiwan Ligand Co., Ltd (Batch number: F171001; Manufacture date: Oct. 5, 2017). Said composition is in the form of lyophilized powder and is prepared as follows. First, ferrous sulfate and glycine (with a purity of more than 98%) were mixed in a weight ratio of 1:1.3 and heated at 60° C. to 90° C. for 8 hours to 48 hours to obtain ferrous amino acid chelate, wherein the chelating ratio of ferrous to amino acid of the ferrous amino acid chelate was between 1:1 and 1:4. Then, the ferrous amino acid chelate was sintered at a temperature ranging from 200° C. to 400° C. to obtain ferrous amino acid chelate particles. The average particle size of the ferrous amino acid chelate particles measured in water by dynamic light scattering (DLS) on Beckman Coulter N5 Submicron Particle Size Analyzer was 1465.90±132.29 nm. The number-average molecular weight (Mn), weight-average molecular weight (Mw), peak average molecular weight (Mp) and polydispersity (PDI) of the ferrous amino acid chelate particles determined by gel permeation chromatography (GPC) using Waters Alliance 2695 System were 68188 Dalton, 525538 Dalton, 286426 Dalton and 7.707205, respectively.

Preparation Example 2: Culture of Human Pancreatic Adenocarcinoma Cell

PANC-1 human pancreatic adenocarcinoma cells were cultured in Dulbecco's Modified Eagle Medium (GIBCO, Invitrogen) containing 10% fetal bovine serum (FBS) (GIBCO, Invitrogen), penicillin, (100 U/mL), and streptomycin (100 µg/mL) in a humidified incubator under 37° C. and 5% $CO_2$. BxPC-3, SUIT-2 and AsPC-1 human pancreatic cancer cells were cultured in RMPI-1640 medium containing 10% fetal bovine serum (FBS) (GIBCO, Invitrogen), penicillin, (100 U/mL), and streptomycin (100 µg/mL) in a humidified incubator under 37° C. and 5% $CO_2$. PANC-1, BxPC-3, and AsPC-1 were purchased from Bioresource Collection and Research Center (Food Industry Research and Development Institute). The identity of SUIT-2 cell line was confirmed by human short tandem repeat (STR) profiling at the Bioresource Collection and Research Center.

Preparation Example 3: Culture of Normal Human Pancreatic Duct Cell

HPDE-E6E7 normal human pancreatic duct epithelial cells (purchased from Expasy; No. CVCL_S972) were cultured in KSF medium containing epidermal growth factor and bovine pituitary extract (Life Technologies, Inc., Grand Island, NY) in a humidified incubator under 37° C. and 5% $CO_2$.

Example 1: Anti-Pancreatic Cancer: Cell Proliferation Assay

MTT assay was used for testing the half maximal inhibitory concentration ($IC_{50}$) of the composition of the present invention. The normal human pancreatic cells (human pancreatic duct epithelial cells) and pancreatic cancer cells (human pancreatic adenocarcinoma cells) obtained from preparation example 2 and preparation example 3 were seeded in a 96-well plate ($4 \times 10^3$ cells/well). The cells were treated with the composition of the present invention obtained from preparation example 1 in a dose-dependent manner ($10^0$, $10^1$, $10^2$, $10^3$, and $10^4$ μg/mL). After incubation for 24, 48, and 72 hours, the MTT reagent was added to each well and then further incubated for 4 hours (37° C. and 5% $CO_2$). Absorbance was measured at 570 nm using a microplate reader (BioTek).

Table 1 below shows the half maximal inhibitory concentration of the human pancreatic duct epithelial cells and human pancreatic cancer cells treated with the composition of the present invention for 24, 48, and 72 hours. Overall, the inhibition of cell proliferation of the composition of the present invention on the pancreatic cancer cells (human pancreatic adenocarcinoma cells) was more significant than that of the normal pancreatic cells.

TABLE 1

The half maximal inhibitory concentration of the pancreatic cancer cells and normal pancreatic cells treated with the composition of the present invention for 24, 48, and 72 hours MTT assays

| Cell line | $IC_{50}$ after treated with the composition of the present invention for 24 hours | $IC_{50}$ after treated with the composition of the present invention for 48 hours | $IC_{50}$ after treated with the composition of the present invention for 72 hours |
|---|---|---|---|
| PANC-1 | 1554.6 ± 214.2 ns | 607.9 ± 168.6* | 352.3 ± 23.8* |
| SUIT-2 | 1127.9 ± 185.7 ns | 661.8 ± 283.9* | 481.3 ± 19.4* |
| AsPC-1 | 905.6 ± 79.2 ns | 676.3 ± 284.3* | 477.3 ± 65.2* |
| BxPC-3 | 1154.6 ± 111.5 ns | 528.5 ± 105* | 322.5 ± 100.9* |
| HPDE-E6E7 | 1201.9 ± 154.3 | 1024.8 ± 146.9 | 700.5 ± 105.6 | ns indicates no significant difference with HPDE-E6E7 group, Student t test
*indicates p < 0.05, Student t test Example 2: Pancreatic Cancer Cell Death Induced by the Composition of the Present Invention Cell death induced by the composition of the present invention was analyzed. The human pancreatic adenocarcinoma cells were seeded in a 6-well plate, and were treated with the composition of the present invention obtained from preparation example 1 in a dose-dependent manner (0, 100, 250, 500, 750 and 1000 μg/mL). After incubation for 48 and 72 hours, the cells were rinsed with PBS buffer, added with trypsin for further treatment, and then were fixed with 70% ethanol under −20° C. for 1 hour. The cells were suspended and stained with PBS containing RNase and propidium iodide. The subG1 phase cells accumulation, which is the characteristics of cell death, was detected by FACSCalibur flow cytometer (Becton Dickinson).

Table 2 below shows the result of analyzing the half maximal inhibitory concentration of said cells. The experimental data shows that the composition of the present invention can inhibit the cell proliferation, and the composition of the present invention can significantly induce cell death of the human pancreatic cancer cells.

TABLE 2

The half maximal inhibitory concentration of the pancreatic cancer cells treated with the composition of the present invention were analyzed by the flow cytometer.

| Cell line | $IC_{50}$ after treated with the composition of the present invention for 48 hours | $IC_{50}$ after treated with the composition of the present invention for 72 hours |
|---|---|---|
| PANC-1 | 571.7 ± 140.9 | 398.7 ± 56.4 |
| SUIT-2 | 688.1 ± 31.8 | 611 ± 78.2 |
| AsPC-1 | 598.4 ± 41.4 | 466.4 ± 19.4 |
| BxPC-3 | 1076.6 ± 109.8 | 660.2 ± 66.9 |

Example 3-1: The Effect of the Composition of the Present Invention on Cell Migration of Human Pancreatic Cancer Cells Transwells with 8.0 μm pore membrane (Corning Costar; Lowell, MA, USA) were placed into a 24-well plate for cell migration assay. The human pancreatic cancer cells obtained from preparation example 2 were used for the cell migration assay. The cells in the control group were not treated with the composition of the present invention, while the cells in experimental groups were treated with the composition of the present invention obtained from preparation example 1 in a dose-dependent manner for 24 hours. The cells of the experimental groups and control group were seeded in the upper chamber with serum-free medium ($2 \times 10^4$ cells/well), and the medium containing 10% FBS was added to the lower chamber as a chemoattractant. After incubation under 37° C. and 5% $CO_2$ for 24 hours, the cells on the lower surface of the pore membranes of the transwells were fixed with methanol, stained with crystal violet (0.05 wt %), and then the cells passing through the pore membranes were counted under a light microscope (40×, three random fields per well) as migrating cell number.

Example 3-2: The Effect of the Composition of the Present Invention on Cell Invasion of Human Pancreatic Cancer Cells Transwells with 8.0 μm pore membrane (Corning Costar; Lowell, MA, USA) were placed into a 24-well plate for cell invasion assay, wherein the pore membrane of the transwells were coated with matrigel (60 μg; BD Bioscience). The human pancreatic cancer cells obtained from preparation example 2 were used for the cell invasion assay. The cells in the control group were not treated with the composition of the present invention, while the cells in experimental groups were treated with the composition of the present invention obtained from preparation example 1 in a dose-dependent manner for 24 hours. The cells of the experimental groups and control group were seeded in the upper chamber with serum-free medium ($1 \times 10^5$ cells/well), and the medium containing 10% FBS was added to the lower chamber as a chemoattractant. After 24 hours incubation, the cells on the lower surface of the pore membranes of the transwells were fixed with methanol, stained with crystal violet (0.05 wt %), and then the cells passing through the pore membranes were counted under a light microscope (40×, three random fields per well) as invading cell number.

The results of examples 3-1 and 3-2 were shown in FIG. 1 to FIG. 4. The inhibition of the cell migration and cell invasion of PANC-1 cell line by the composition of the present invention was dose-dependent. The cell motility of the SUIT-2 cells shown in FIG. 2, the BxPC-3 cells shown in FIG. 3, and the AsPC-1 cells shown in FIG. 4 was inhibited by the composition of the present invention. The aforementioned results show that the composition of the present invention plays an important role in inhibiting the motility of cancer cells.

Example 4: Inhibiting the Tumor Growth of Orthotopic Xenograft Pancreatic Cancer by the Composition of the Present Invention The human pancreatic adenocarcinoma cell line PANC-1 obtained from preparation example 2 was cloned and labelled with luminescence and fluorescence vector by common skills. The luminescence and fluorescence-labelled cells were implanted into pancreas of experimental mice (60 NOD-SCID experimental mice purchased from BioLASCO Taiwan Co., Ltd) with a cell number of $5 \times 10^5$ by surgery. 10 days after the cell implantation to the pancreas of the animals, the baseline data was measured by noninvasive in vivo imaging system (IVIS). After the baseline IVIS data were obtained, all the experimental mice were randomly and evenly assigned into groups [the value of mean±3 s.d. of measured IVIS data was calculated, and the animals having an IVIS data within the standard range were assigned into control group, low-dose group of the composition of the present invention from preparation example 1 (24 mg/kg), and high-dose group of the composition of the present invention (72 mg/kg)]. After division into groups, the drugs were administrated. The physiological saline and the composition of the present invention at two concentrations dissolved in the physiological saline were administrated respectively and directly into the stomachs of the mice through feeding tubes. The mice administered with the composition of the present invention were continuously observed for the drug toxicity, and measured for body weight for one month, and measured for the IVIS data for four weeks. Once the mice died, or severe irreversible toxicity or server ascites was caused, said mice had to be sacrificed and considered as a time point of event, for calculating the difference of the survival rate. Regarding the groups of the experiment, there were 13 orthotopic xenograft pancreatic cancer mice in each of the control group, the high-dose group, and the low-dose group (comprising 3 experimental mice for quantitative measurement of the malignant ascites in each group), after excluding the mice that died during the experiment and the mice with too high or too low IVIS data (outlier). The time points of IVIS data measurement were the following 7 time points: Baseline 10 Day (Baseline 10D), the $13^{th}$ day (13D), the $17^{th}$ day (17D), the $20^{th}$ day (20D), the $24^{th}$ day (24D), the $31^{st}$ day (31D), and the $38^{th}$ day (38D) of experiment. IVIS data were measured twice a week after administration in the first two weeks, mainly for observing the therapeutic effect variation of the composition of the present invention on the pancreatic cancer in the initial stage. In the last two weeks, the IVIS data measurement was adjusted to once a week. Regarding the administration of the present invention to the experimental mice, the composition of the present invention was continuously administered for 90 days and then withdrawn. The adopted dosage regimen was mainly determined by the fact that the control group of the orthotopic xenograft pancreatic cancer mice survived for around 90 days when the cell number of the implanted PANC-1 was $5 \times 10^5$. The survival period of each mouse during the experimental period was recorded.

As shown in FIG. 5A to FIG. 5G and FIG. 6, the two experimental groups (high-dose group and low-dose group) of the orthotopic xenograft pancreatic cancer mice treated with the composition of the present invention showed significant effect on tumor growth inhibition of the orthotopic xenograft pancreatic cancer after the $24^{th}$ day of the experiment (24D) compared to the control group. The difference of detection signals was increased and the maximum difference of detection signals was reached on the $38^{th}$ day of the experiment. There were no significant differences between the IVIS data of the high-dose group and the low-dose group. Therefore, the use of the composition of the present invention can inhibit the tumor growth of the orthotopic xenograft pancreatic cancer mice implanted with PANC-1 cell line.

For further observing the therapeutic effect of the composition of the present invention on the pancreatic cancer, the comparison of IVIS data of two experimental groups (high-dose group and low-dose group) and control group on every time point of measurement were made as the following Table 3. As shown in the following Table 3, after the third day after treatment with the composition of the present invention (D13, i.e. the $13^{th}$ day of the experiment), it could be observed that the tumor growth of the pancreatic cancer of two experiment groups was slower than that of the control group on each IVIS data measurement time point. Therefore, the composition of the present invention has the effect of inhibiting the tumor growth of the pancreatic cancer. Besides, on the last measurement time point of IVIS data (38D), it could be seen that the composition of the present invention had 50%-60% inhibition on the growth of pancreatic cancer in the two experimental groups.

TABLE 3

The comparison of experimental groups and the control group of the composition of the present invention on each measurement time point of IVIS data

| Measurement time point | Group | | |
| --- | --- | --- | --- |
| | Control group | Low-dose group (24 mg/kg) | High-dose group (72 mg/kg) |
| Baseline 10 D | 1 ± 0.44 | 0.93 ± 0.46 | 0.92 ± 0.40 |
| The $13^{th}$ day of experiment (13 D) | 1 ± 0.28 | 0.62 ± 0.32 | 0.77 ± 0.26 |
| The $17^{th}$ day of experiment (17 D) | 1 ± 0.13 | 0.55 ± 0.21 | 0.66 ± 0.41 |
| The $20^{th}$ day of experiment (20 D) | 1 ± 0.22 | 0.60 ± 0.20 | 0.50 ± 0.23 |
| The $24^{th}$ day of experiment (24 D) | 1 ± 0.35 | 0.37 ± 0.12 | 0.48 ± 0.14 |
| The $31^{st}$ day of experiment (31 D) | 1 ± 0.24 | 0.38 ± 0.09 | 0.38 ± 0.13 |
| The $38^{th}$ day of experiment (38 D) | 1 ± 0.22 | 0.38 ± 0.08 | 0.44 ± 0.14 |

Figure 7:
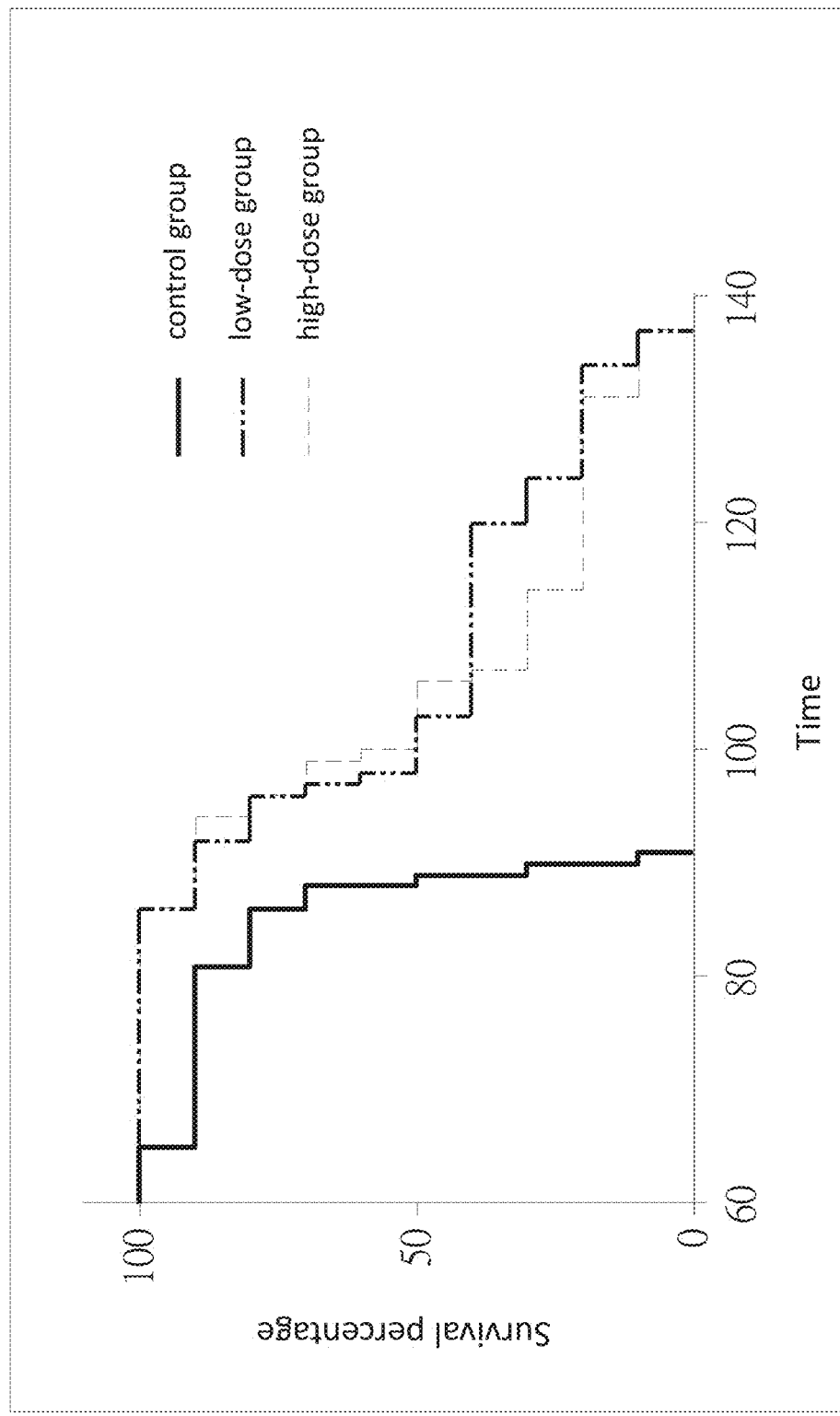
FIG. 7 is the survival chart of the orthotopic xenograft pancreatic cancer mice in high-dose group and low-dose group of the composition of the present invention.

Besides, the differences of the survival period of the two experimental groups of the high-dose group and the low-dose group and the control group were shown in FIG. 7.

Among the ten mice of the control group, the first dead mouse was found on the 65$^{th}$ day of the experiment, massive death continually occurred in the mice of the control group after the 80$^{th}$ day of the experiment, and then the last mouse of the control group died on the 91$^{st}$ day of the experiment. The average survival period of the control group was 85.7 days. Regarding the survival period of the ten mice treated with the composition of the present invention in either of the two experimental groups of the high-dose group and low-dose group, the first dead mice in each of the two groups were both found on the 86$^{th}$ day of the experiment; and the trends of survival period of both two groups fell consistently and slowly. Therefore, after treated with the composition of the present invention for 90 days, both the high-dose group and the low-dose group showed the same therapeutic effect on extension of survival period of experimental orthotopic xenograft pancreatic cancer mice. The longest survival period of the two experimental groups treated with the composition of the present invention appeared on the 137$^{th}$ day. The average survival period of the low-dose group was 108.7 days, while the average survival period of the high-dose group was 107 days. The average survival period of the high-dose group was 22 days longer than that of the control group.

Example 5: The Effect of the Composition of the Present Invention on the Ascites from Pancreatic Cancer The mice which were reserved from example 4 for quantitative experiment were used for observing the malignant ascites from pancreatic cancer. There were three mice in each of the three following groups: two experimental groups (high-dose group and low-dose group of the composition obtained from preparation example 1) and the control group. The body weight of the mice was measured and the appearance and the activity of the mice were observed every day. The mice were dissected on the 90 days of the experiment for quantifying the malignant ascites from pancreatic cancer.

Figure 8:
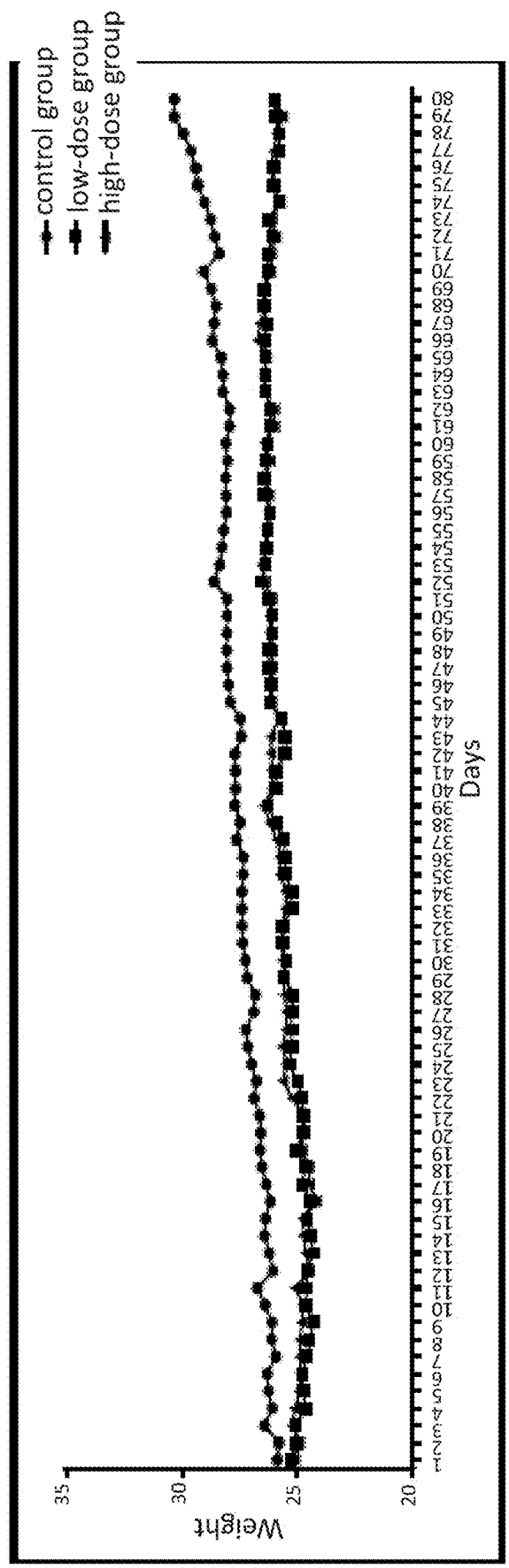
FIG. 8 shows the quantitative measurement of malignant ascites of orthotopic xenograft pancreatic cancer mice in high-dose group and low-dose group of the composition of the present invention.
Figure 9:
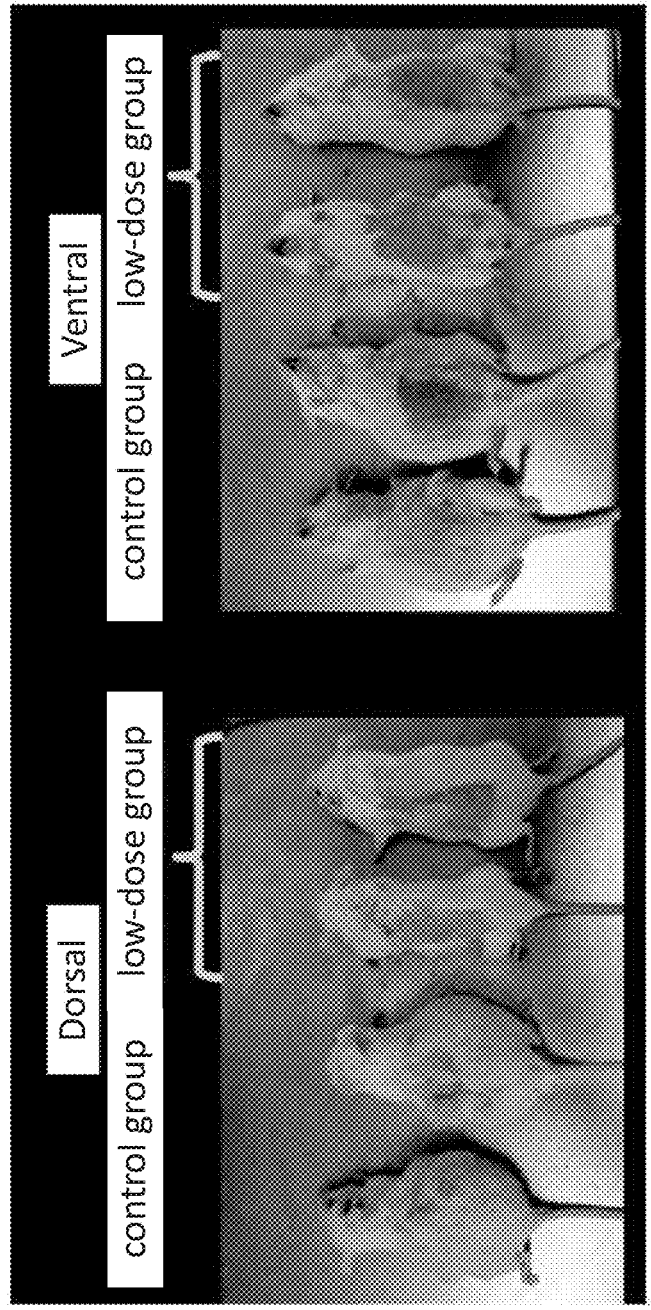
FIG. 9 shows the dorsal and ventral appearances of the experimental mice in the low-dose group of the composition of the present invention before dissection.
Figure 10A:
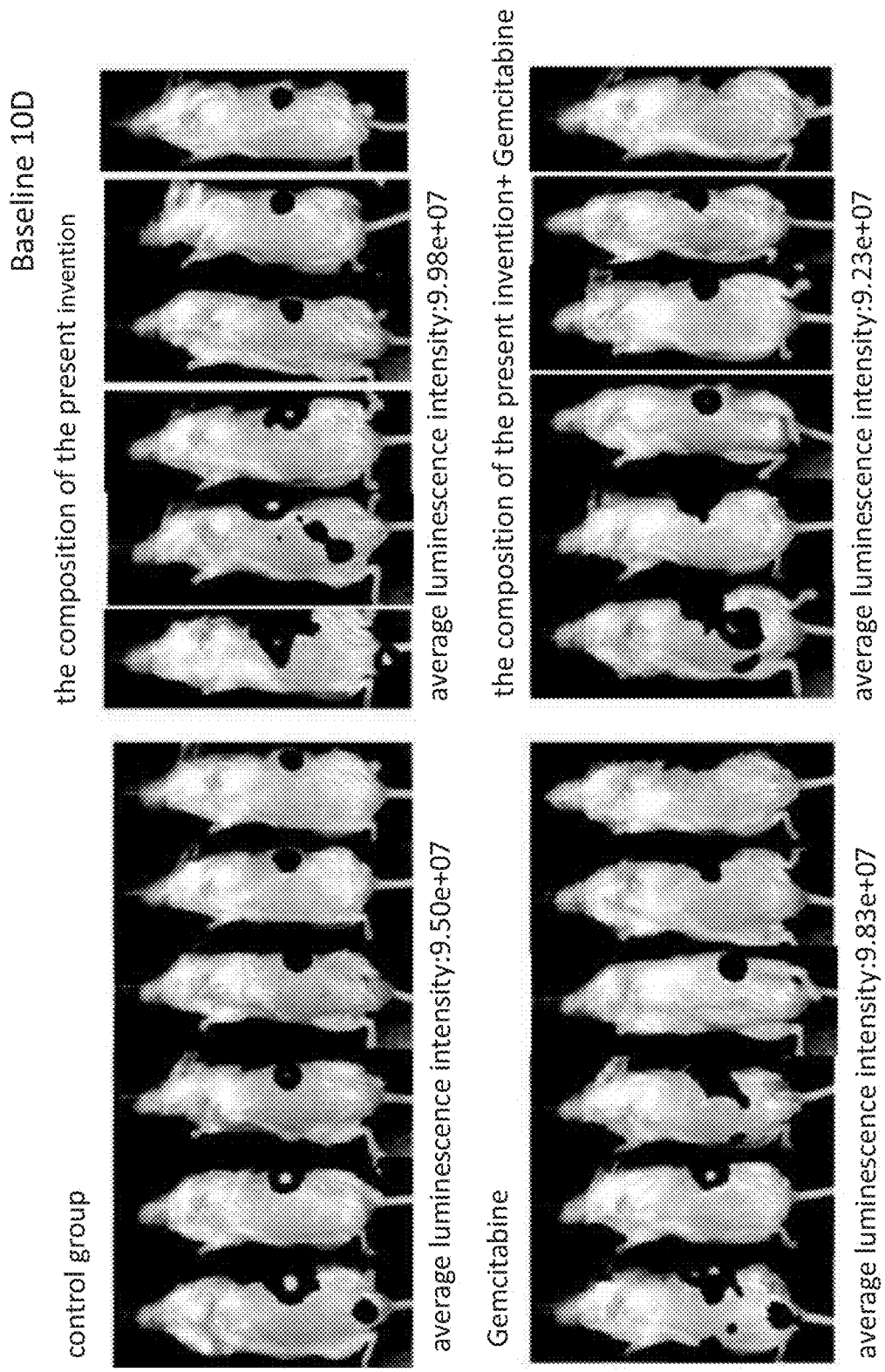
FIG. 10A is the bioluminescence image of the pancreatic cancer tumor treated with the composition of the present invention, gemcitabine or the combination thereof at Baseline 10D.
Figure 10B:
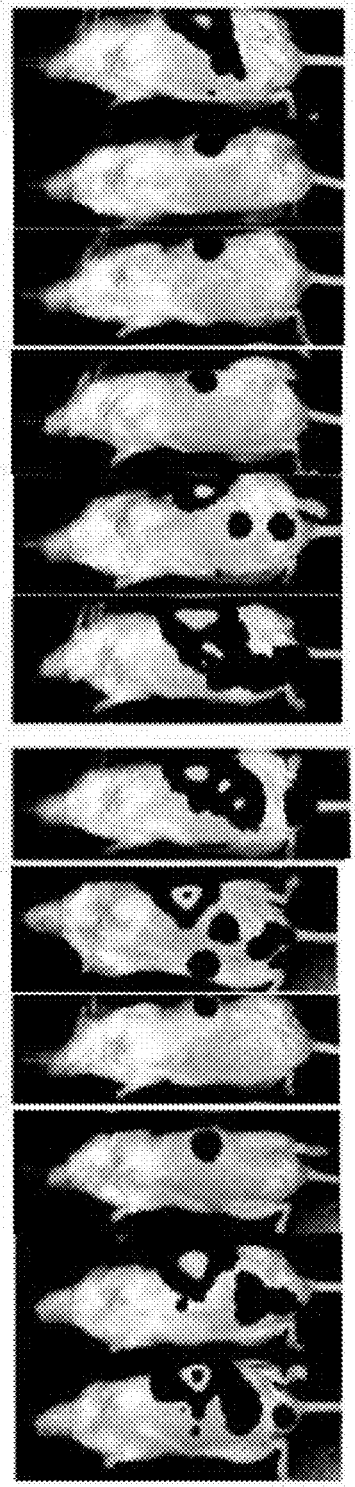
FIG. 10B is the bioluminescence image of the pancreatic cancer tumor treated with the composition of the present invention, gemcitabine or the combination thereof on the $17^{th}$ day of experiment.
Figure 10B:
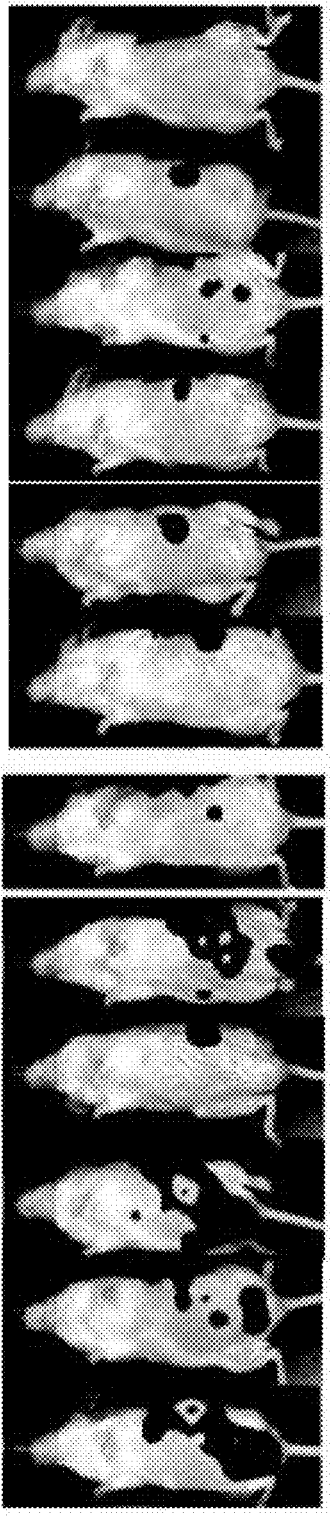
Figure 10C:
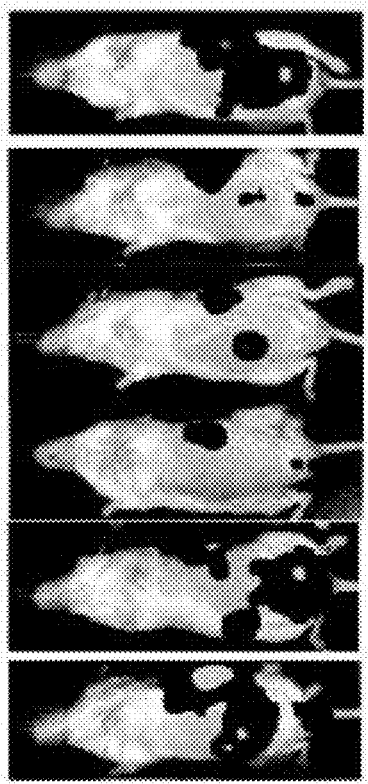
FIG. 10C is the bioluminescence image of the pancreatic cancer tumor treated with the composition of the present invention, gemcitabine or the combination thereof on the $24^{th}$ day of experiment.
Figure 10C:
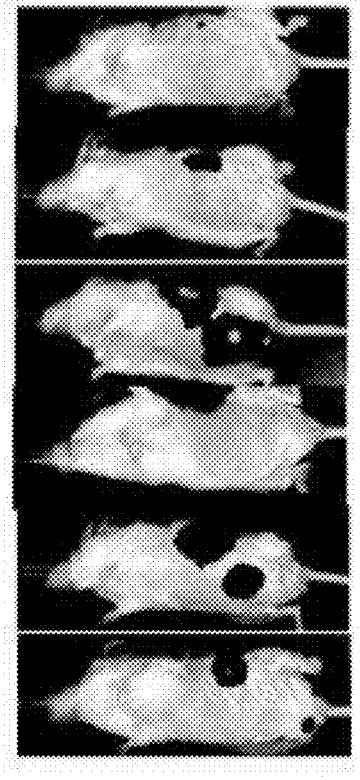
Figure 10C:
Figure 10C:
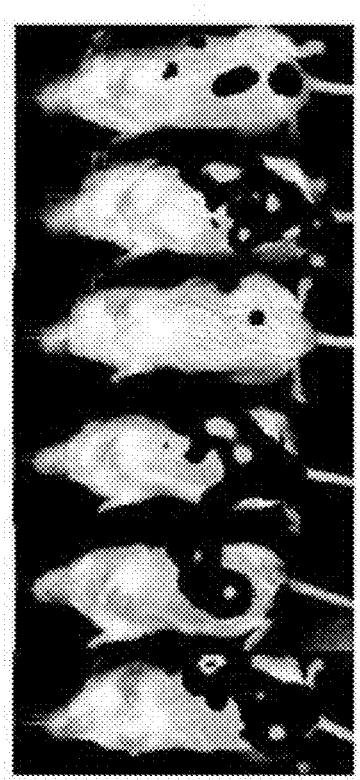
Figure 10D:
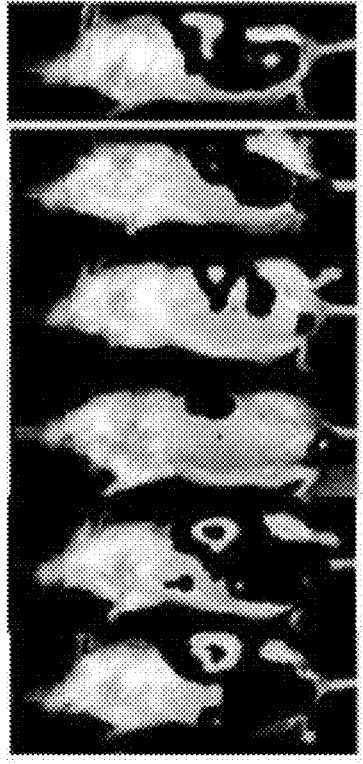
FIG. 10D is the bioluminescence image of the pancreatic cancer tumor treated with the composition of the present invention, gemcitabine or the combination thereof on the $31^{st}$ day of experiment.
Figure 10D:
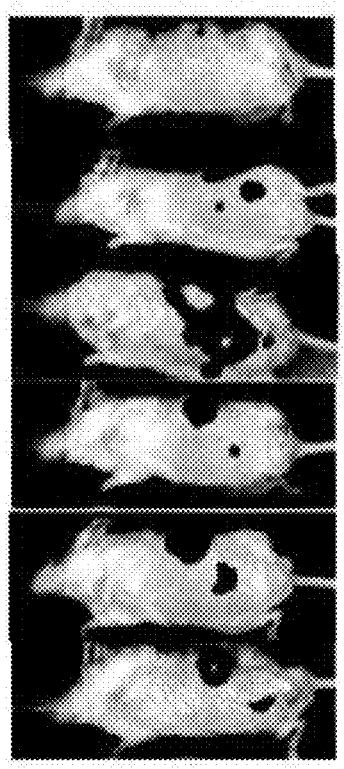
Figure 10D:
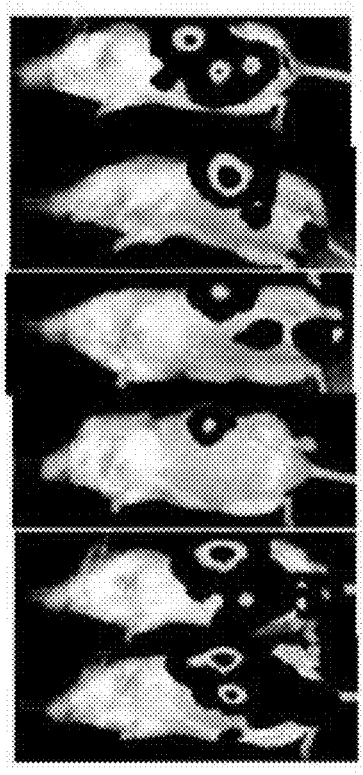
Figure 10D:
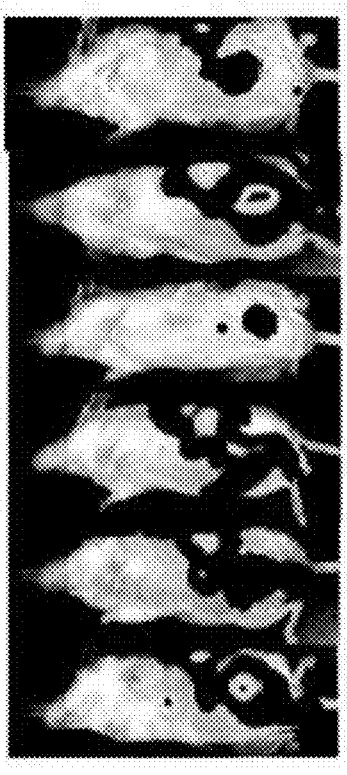
Figure 10E:
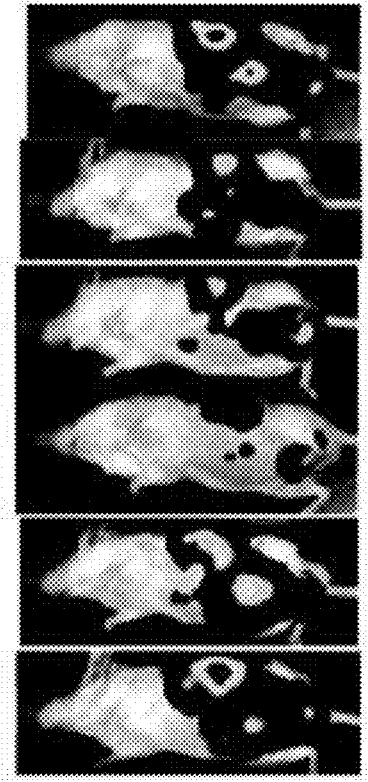
FIG. 10E is the bioluminescence image of the pancreatic cancer tumor treated with the composition of the present invention, gemcitabine or the combination thereof on the $38^{th}$ day of experiment.
Figure 10E:
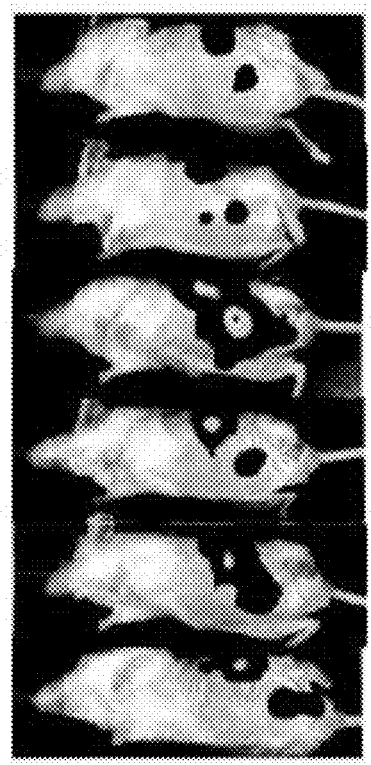
Figure 10E:
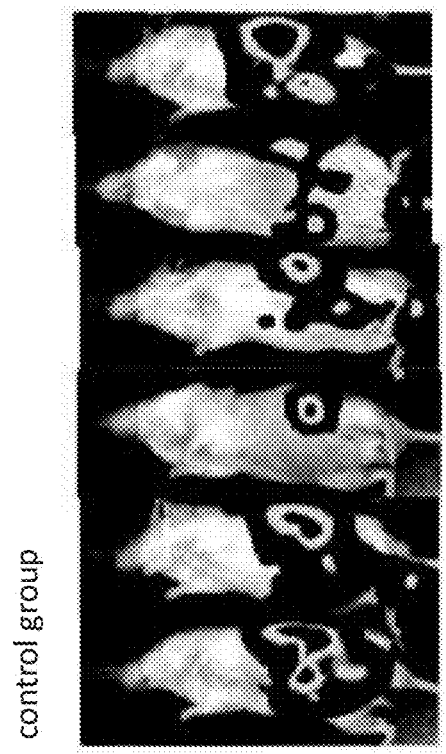
Figure 10E:
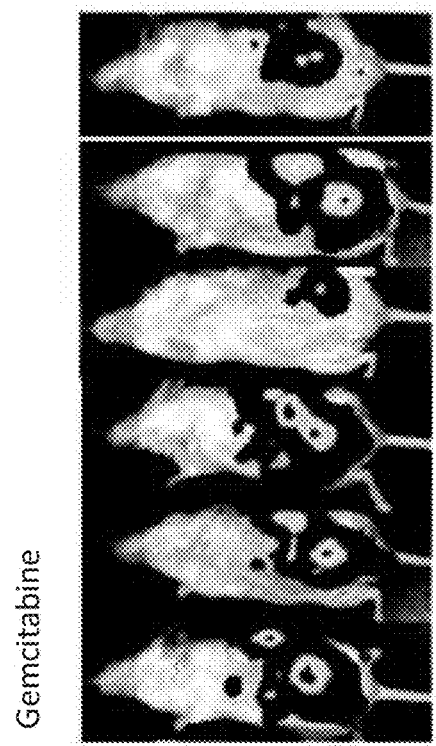
Figure 11:
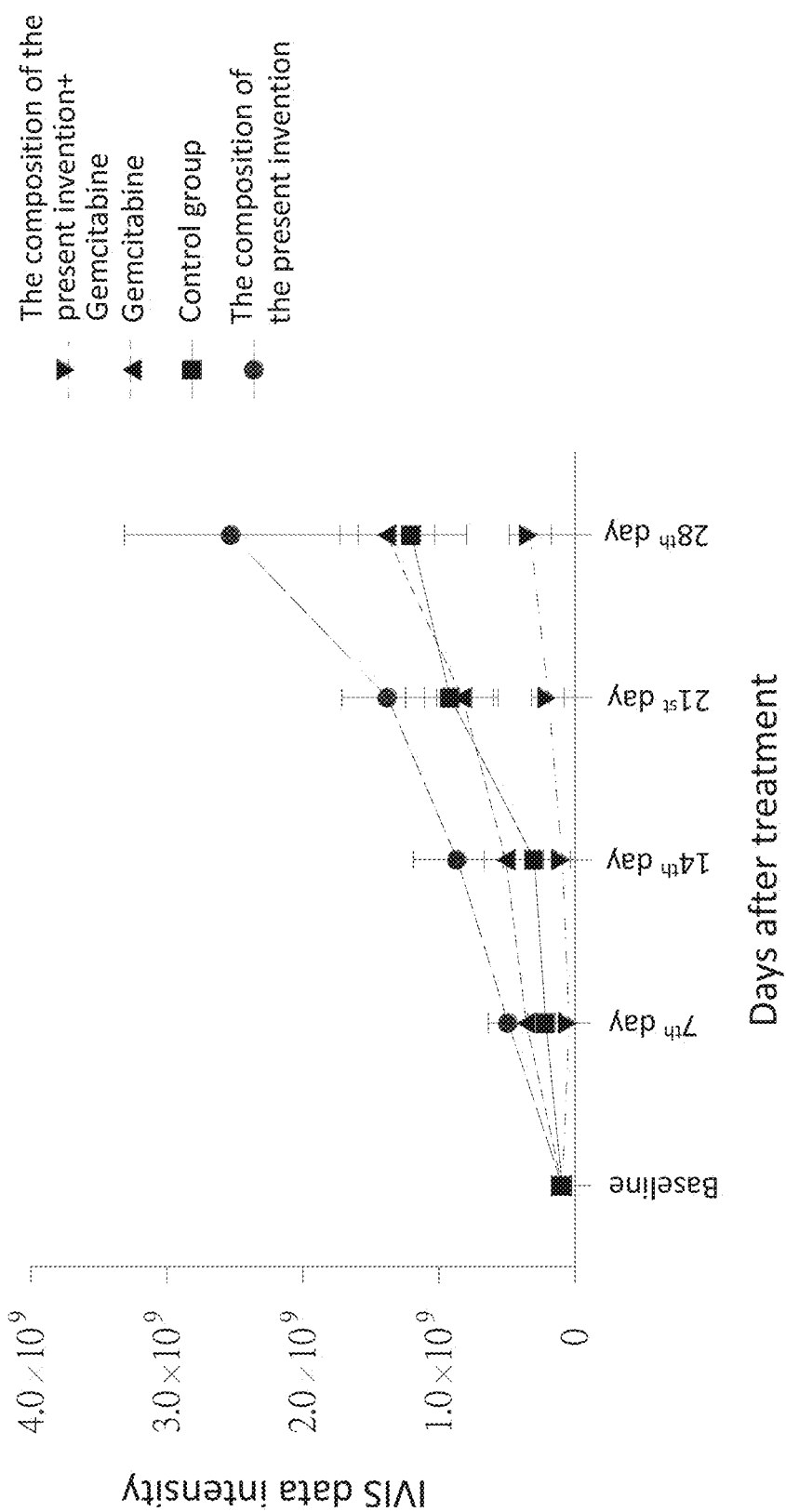
FIG. 11 is the run chart of the pancreatic cancer tumor development after treated with the composition of the present invention, gemcitabine, or the combination thereof.

FIG. 8 shows the body weight variation of each group during the 80 days after treated with the composition of the present invention (i.e. the 90 days of the experiment). During the 80-day period treating with the composition of the present invention, the average body weight of the two groups, the high-dose group and the low-dose group, did not fluctuate dramatically. The average body weight of the control group on around the 70$^{th}$ day after treatment (the 80$^{th}$ day of the experiment) increased sharply and the average body weight on the 80$^{th}$ day after treatment (the 90$^{th}$ day of the experiment) increased almost 3 grams. FIG. 9 shows the photos of the control group and the low-dose group treated with the composition of the present invention on the 90$^{th}$ day of the experiment, before the dissection. The abdominal cavities of the mice in the control group were abnormally swollen, but the abdominal cavities of the experimental animals in the low-dose group treated with the composition of the present invention were not significantly different. According to the observation of ascites extent, the abdominal cavity of dissected mice of the control group was full of the ascites, while the mice of the low-dose group of the composition of the present invention did not show this situation. The quantitative measurement result of the mice of the control group and the low-dose group showed that the average amount of ascites in the control group was 6 mL, while the average amount of ascites in the low-dose group treated with the composition of the present invention was around 1 mL. There was a huge difference between the quantitative measurement result of orthotopic xenograft pancreatic cancer mice of the control group and the low-dose group treated with the composition of the present invention, which meant that the composition of the present invention had the effect of mitigating or inhibiting the production of malignant ascites of advanced stage on orthotopic xenograft pancreatic cancer mice. Besides, based on the observation whether the experimental mice had the side effect or not from the beginning of experiment to the 90$^{th}$ day of the experiment, the body weight, the appearance, and the activity of experimental mice showed no significant changes. Therefore, it can be deduced that the composition of the present invention has no significant side effect on the orthotopic xenograft pancreatic cancer mice.

Example 6: The Therapeutic Effect (I) of Combination of Gemcitabine and the Composition of the Present Invention on the Orthotopic Xenograft Pancreatic Cancer The human pancreatic adenocarcinoma cell line PANC-1 obtained from preparation example 2 was cloned and labelled with luminescence and fluorescence vector. The luminescence and fluorescence-labelled cells were implanted into pancreas of experimental mice (50 NOD-SCID experimental mice purchased from BioLASCO Taiwan Co., Ltd) with a cell number of $5 \times 10^5$ by surgery. 10 days after the cell implantation to the pancreas of the animals, the baseline data was measured by noninvasive in vivo imaging system (IVIS). After the baseline IVIS data were obtained, all the experimental mice were randomly and evenly assigned into groups [the value of mean±3 s.d. of measured IVIS data was calculated, and the animals having an IVIS data within the standard range were assigned into control group (physiological saline was used), the group of the composition of the present invention obtained from preparation example (24 mg/kg the composition obtained for preparation example 1 was administrated directly into the stomachs of the mice through feeding tubes once per day), gemcitabine group (100 mg/kg gemcitabine was administered by intravenous injection twice per week), and combination group (24 mg/kg the composition of the present invention was administered daily and 100 mg/kg gemcitabine was administered twice per week), followed by the administration. The dosage and dosage regimen of the composition of the present invention were decided based on the results of example 4 that there were no significant differences between the high-dose group and the low-dose group, so the dosage of 24 mg/kg was chosen for this experiment. The dosage and the dosage regimen of first-line drug for the pancreatic cancer were decided in accordance with two journal articles: Cook, Natalie, et al. "Gamma secretase inhibition promotes hypoxic necrosis in mouse pancreatic ductal adenocarcinoma." Journal of Experimental Medicine 209.3 (2012): 437-444. and Olive, Kenneth P., et al. "Inhibition of Hedgehog signaling enhances delivery of chemotherapy in a mouse model of pancreatic cancer." Science (2009), so that the gemcitabine was administered at the dosage of 100 mg/kg twice per week for the experiment. The time points of IVIS data measurement were: Baseline 10 Day (Baseline 10D), the 17$^{th}$ day (the 7$^{th}$ day after administration), the 24$^{th}$ day (14 days after treatment), the 31$^{st}$ day (21 days after treatment), and the 38$^{th}$ day (28 days after treatment) of the experiment. The blood tests for total bilirubin (T-bilirubin), glutamate oxaloacetate transaminase/aspartate aminotransferase (GOT/AST), and glutamate pyruvate transaminase/alanine transaminase (GPT/ALT) of all experimental animals on the 9th week were conducted and the mice were observed whether the jaundice occurred or not by the naked eyes. The jaundice signs of mice which could be observed by naked eyes included: emaciation, swollen gall, yellow dark skin, and abnormal yellow limbs and tail. The survival period of each mouse during the experiment was recorded.

As shown in FIG. 10A to FIG. 10E and FIG. 11, the group of the composition of the present invention had significant effect of inhibiting the tumor growth of the pancreatic cancer compared to the control group. Besides, the effect is similar to the effects shown in the experimental groups of the high-dose group (72 mg/kg) and the low-dose group (24 mg/kg) of example 5, with a therapeutic effect of around 50% in inhibiting the tumor growth of the pancreatic cancer. The effect of inhibiting the tumor growth of orthotopic xenograft pancreatic cancer in the gemcitabine group 28 days after treatment was similar to the effects shown in the group of the composition of the present invention; and the trend of the measurement result of the IVIS data was also consistent with that during the period of the experiment, with a therapeutic effect of around 50% in inhibiting the tumor growth of the pancreatic cancer. The effect of inhibiting the tumor growth of orthotopic xenograft pancreatic cancer in the combination group 28 days after treatment was better than that of the group of the composition of the present invention and the gemcitabine group, having the effect of inhibiting tumor growth of the pancreatic cancer of 80%, which was higher than that of the control group. Therefore, the combination of the composition of the present invention and the gemcitabine, the clinical first-line drug of pancreatic cancer, has the better effect in the inhibition the tumor growth of the orthotopic xenograft pancreatic cancer.

Figure 12:
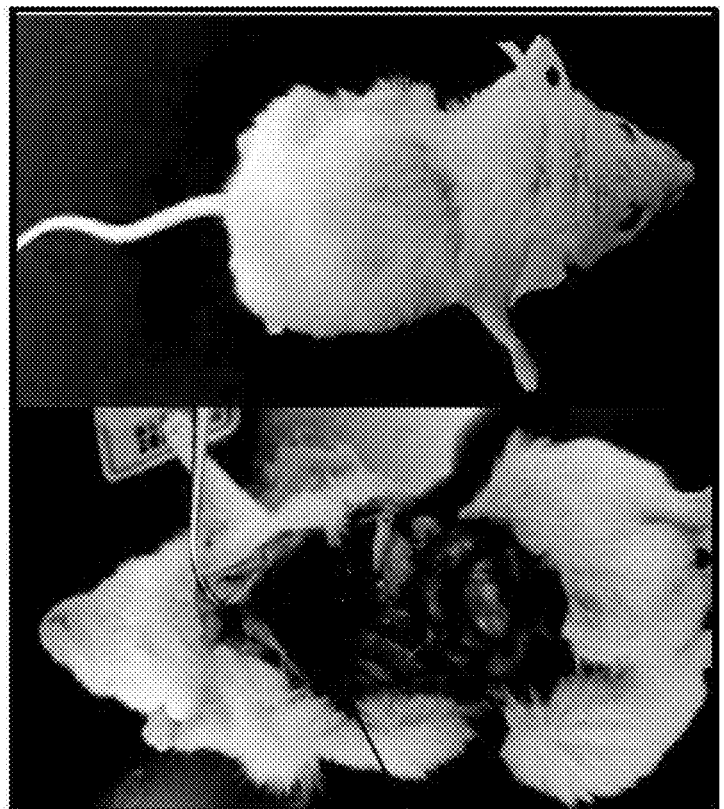
FIG. 12 is dissection photos showing the jaundice phenomenon of the mouse treated with the combination of the composition of the present invention and gemcitabine for the pancreatic cancer tumor on the 9$^{th}$ week of treatment.
Figure 13A:
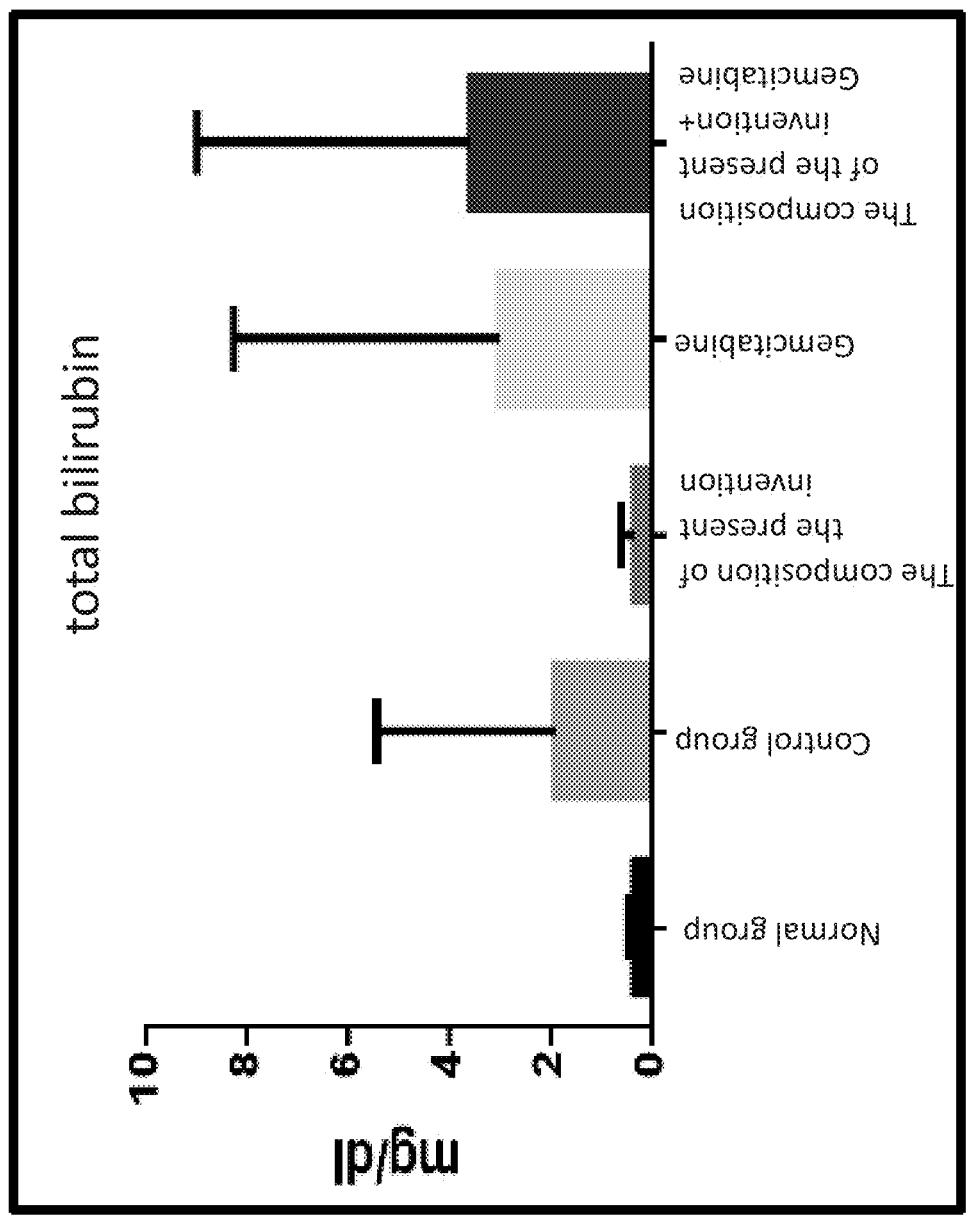
FIG. 13A shows the total bilirubin levels in blood samples of each group of experimental animals which were treated with: the composition of the present invention, gemcitabine, or the combination thereof for the pancreatic cancer tumor.
Figure 13B:
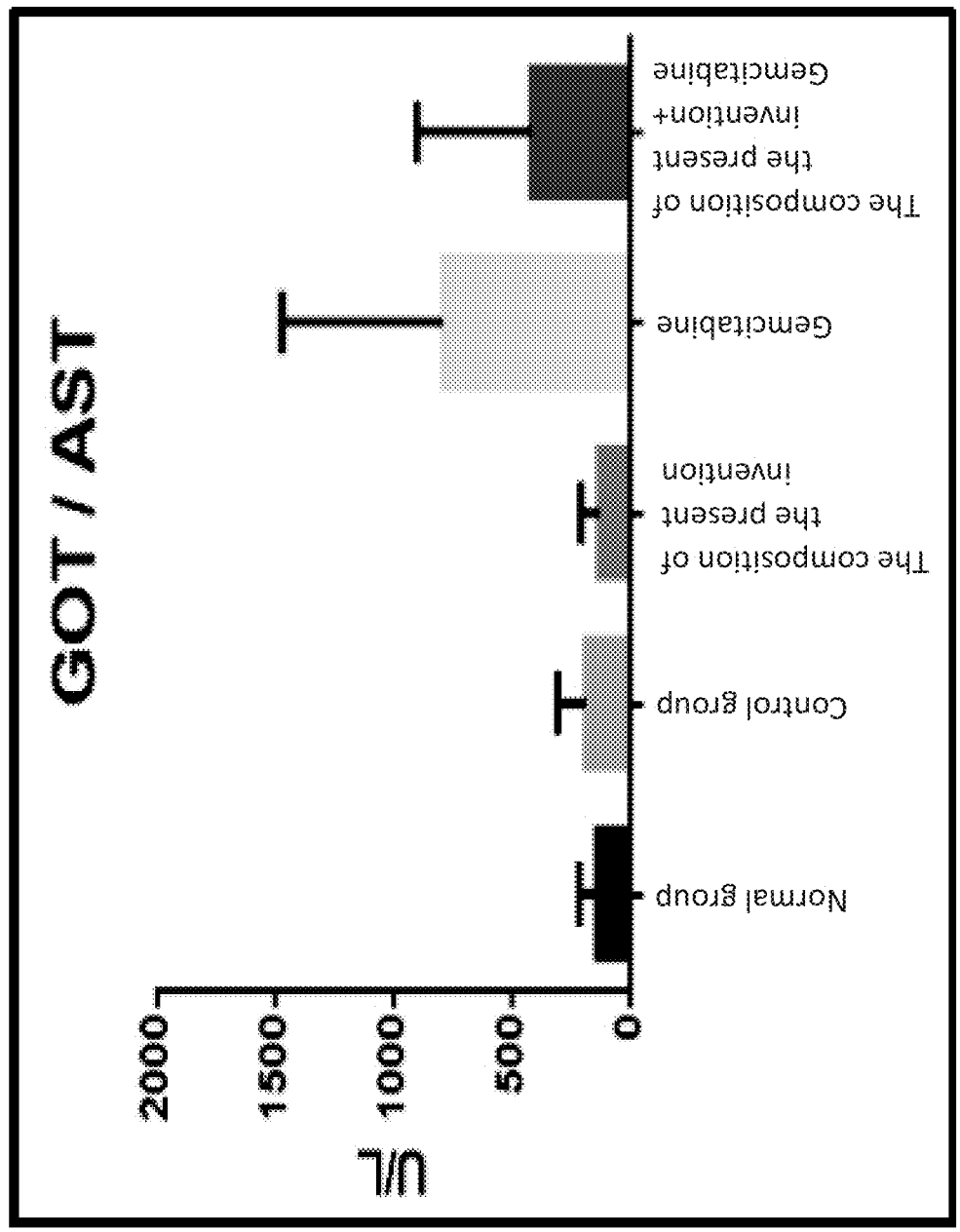
FIG. 13B shows the GOT/AST levels in blood samples of each group of experimental animals which were treated with: the composition of the present invention, gemcitabine, or the combination thereof for the pancreatic cancer tumor.
Figure 13C:
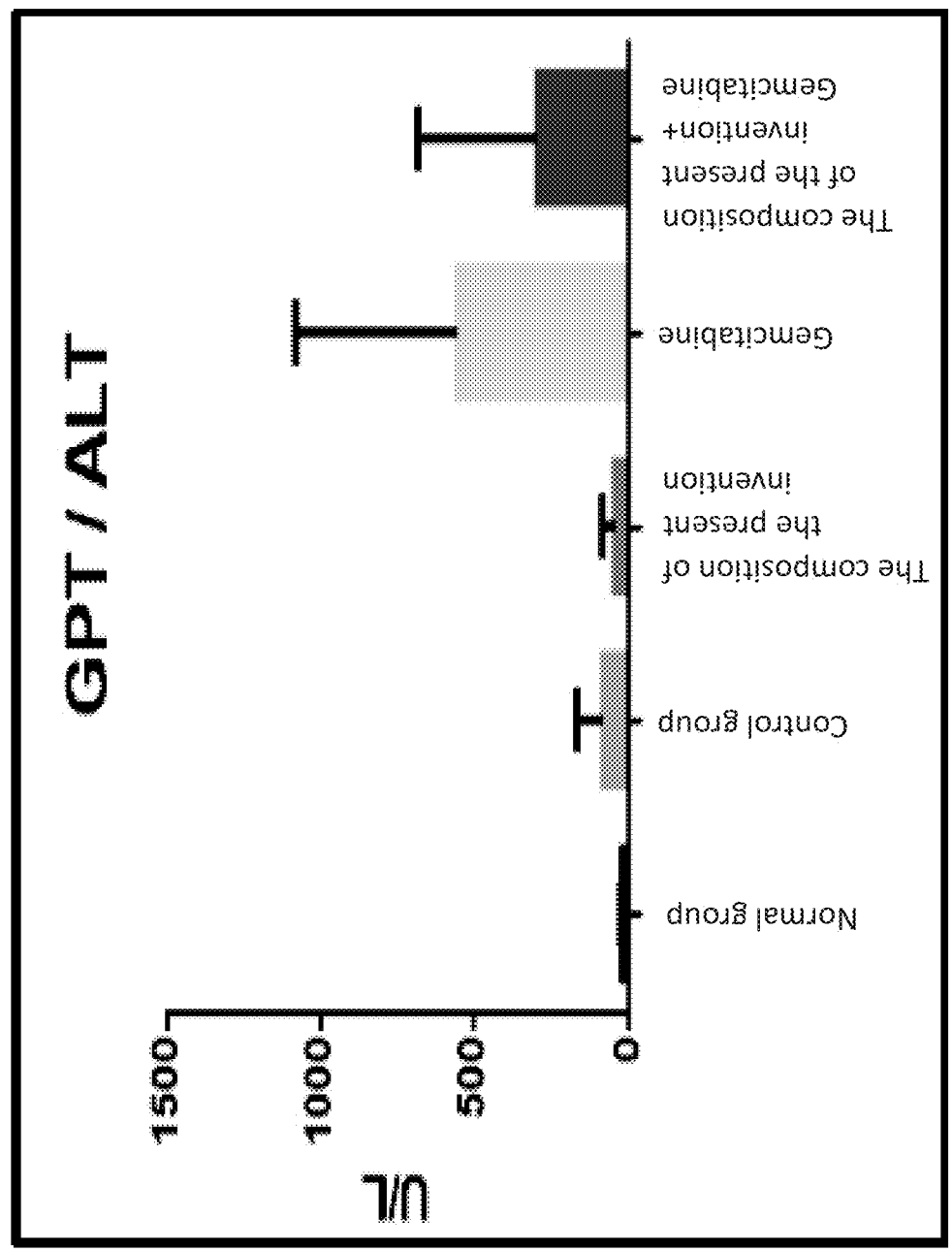
FIG. 13C shows the GPT/ALT levels in blood samples of each group of experimental animals which were treated with: the composition of the present invention, gemcitabine, or the combination thereof for the pancreatic cancer tumor.
Figure 14:
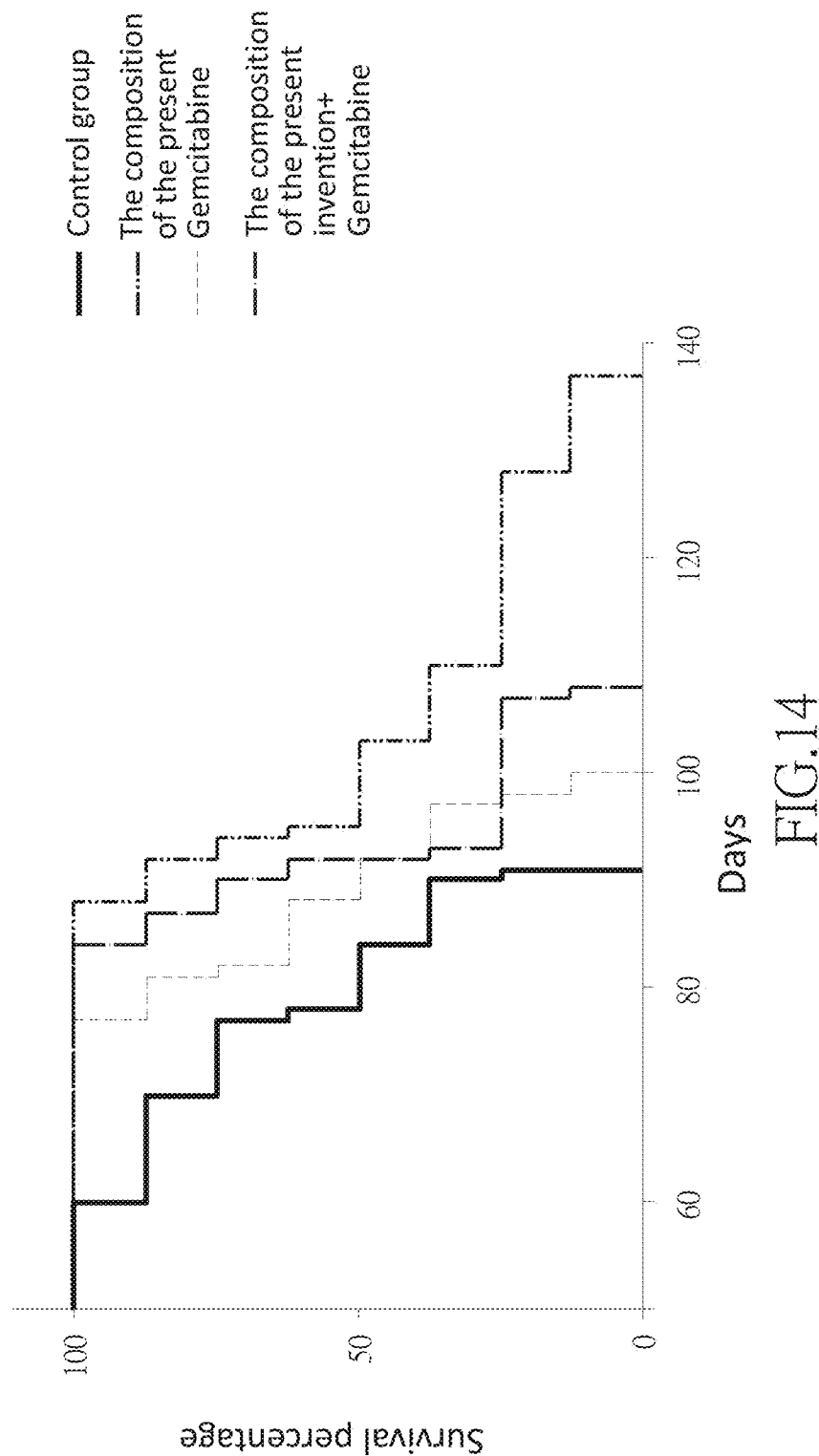
FIG. 14 is the survival chart of the experimental animals treated with the composition of the present invention, gemcitabine, or the combination thereof for the pancreatic cancer treatment.
Figure 15A:
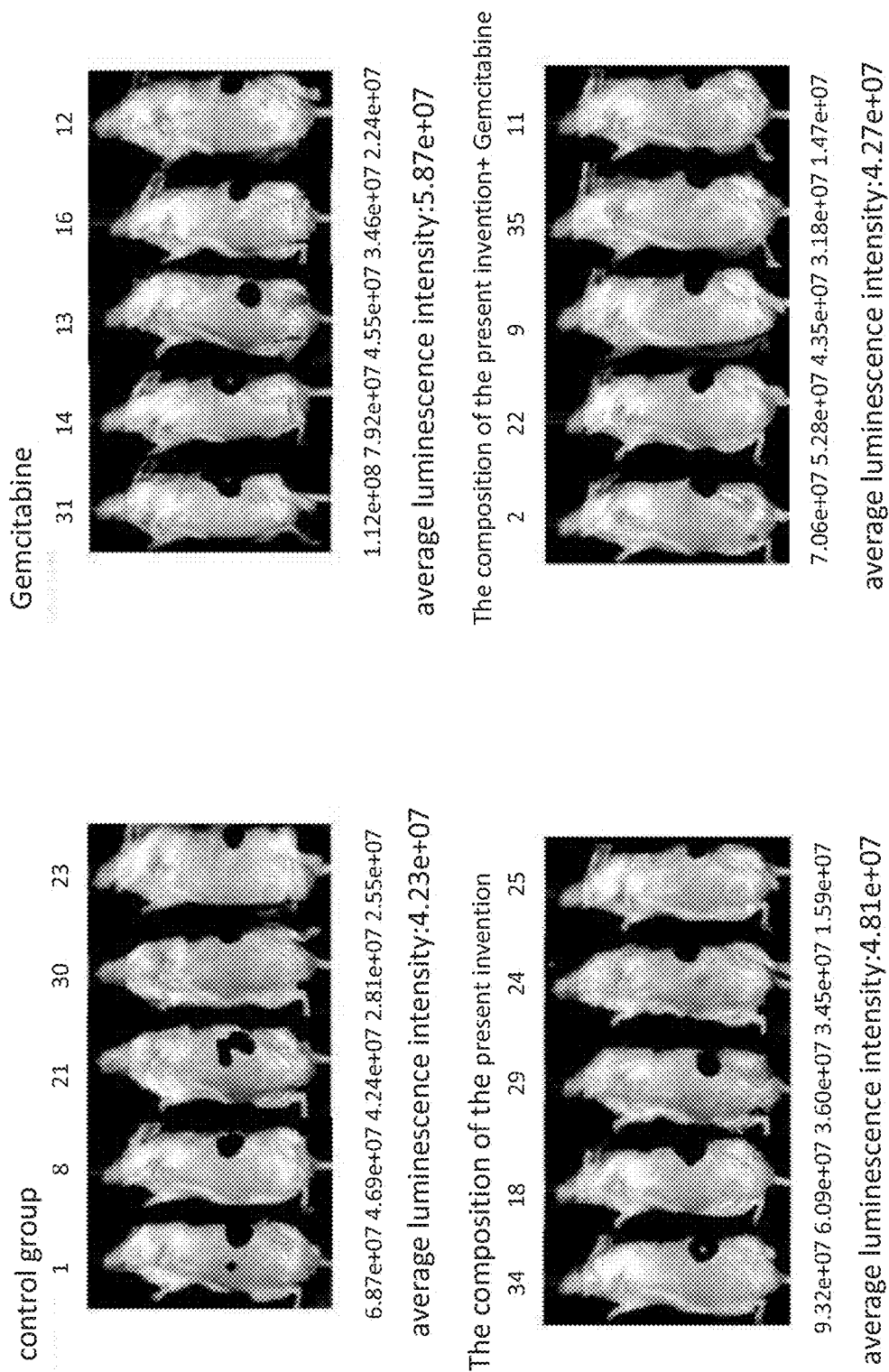
FIG. 15A is the bioluminescence image of the pancreatic cancer tumor with the treatment (II) of the composition of the present invention, gemcitabine, or the combination thereof at Baseline 10D.
Figure 15B:
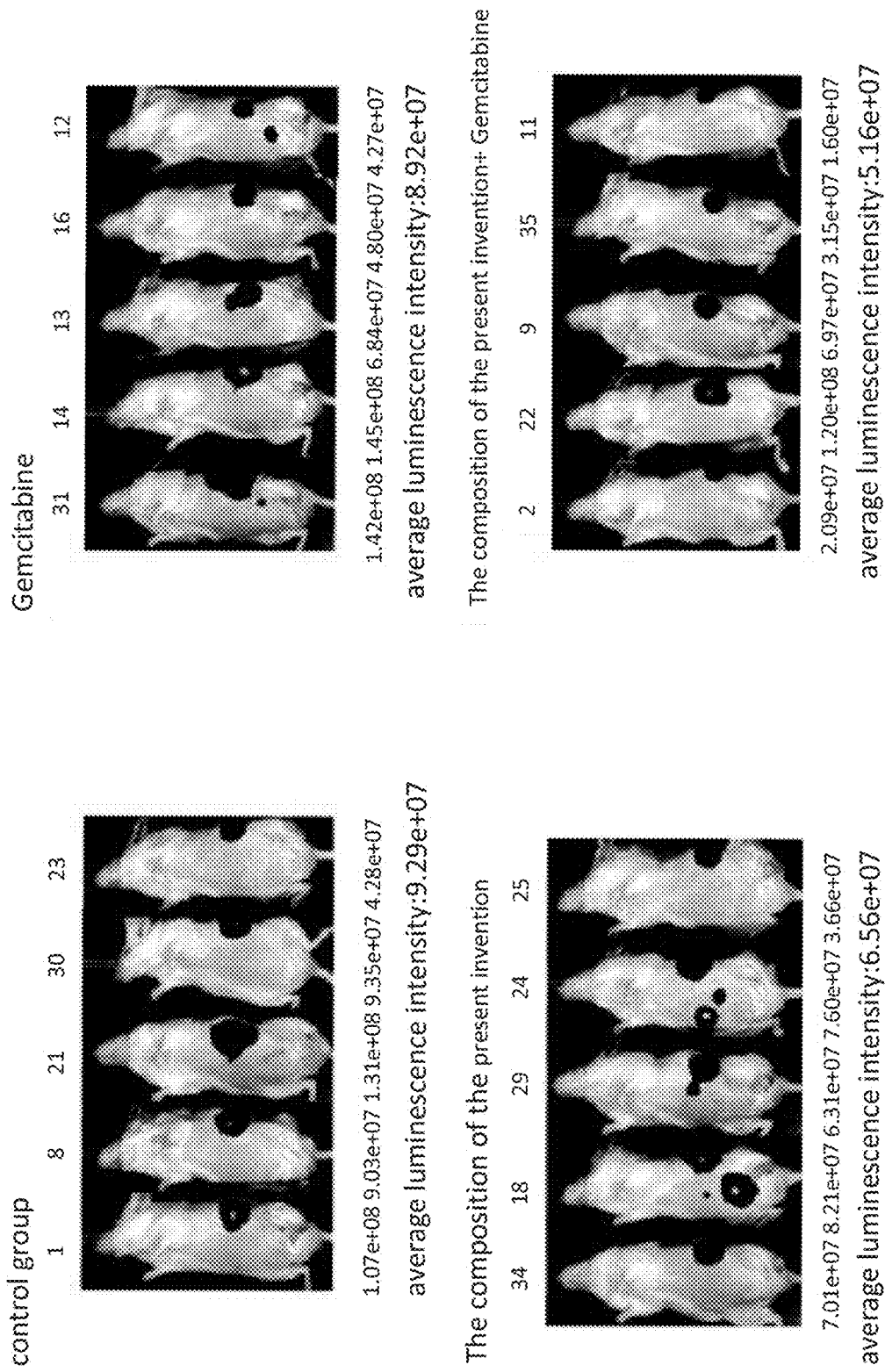
FIG. 15B is the bioluminescence image of the pancreatic cancer tumor with the treatment (II) of the composition of the present invention, gemcitabine, or the combination thereof on the 17$^{th}$ day of experiment.
Figure 15C:
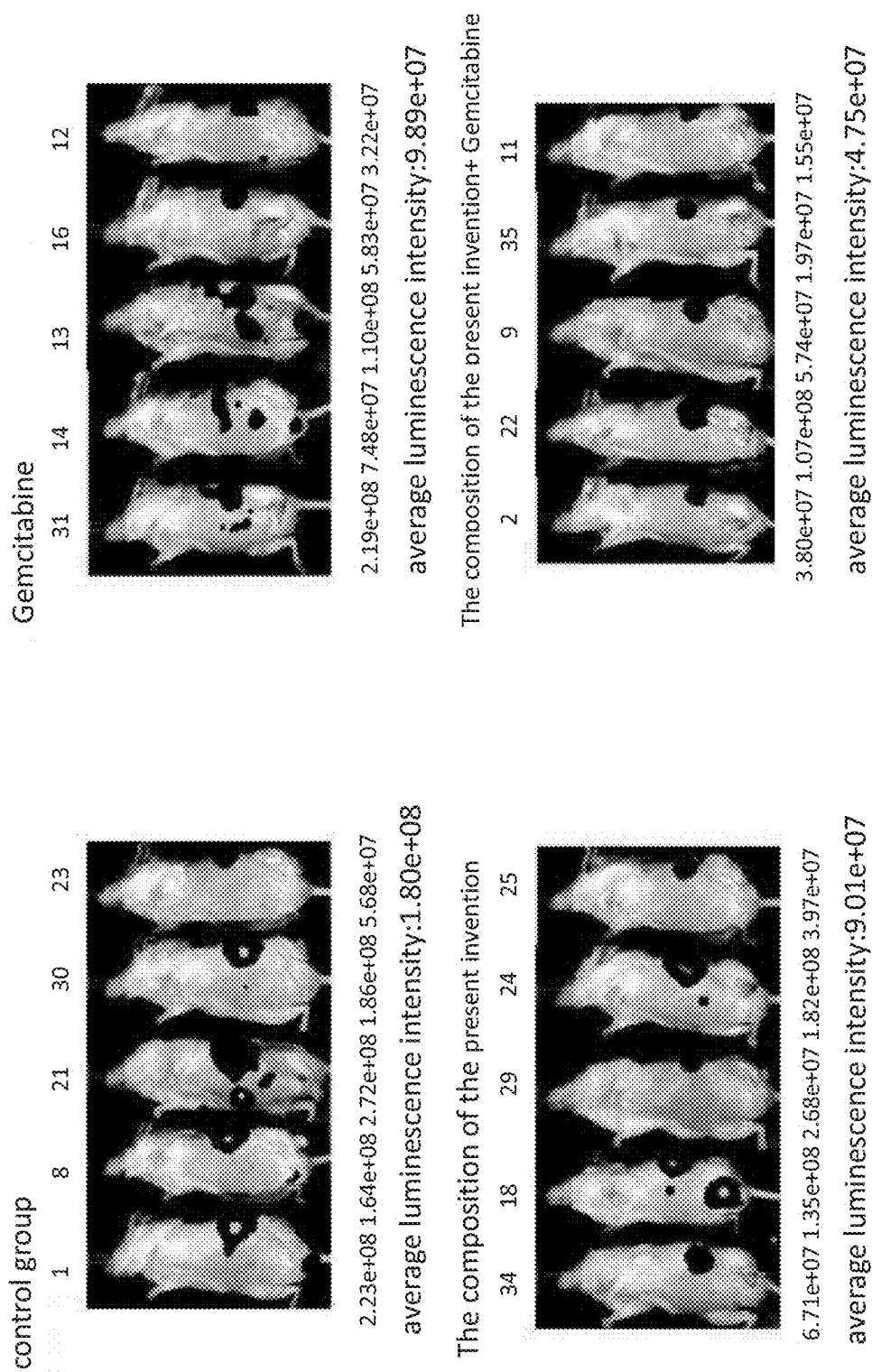
FIG. 15C is the bioluminescence image of the pancreatic cancer tumor with the treatment (II) of the composition of the present invention, gemcitabine, or the combination thereof on the 24$^{th}$ day of experiment.
Figure 15D:
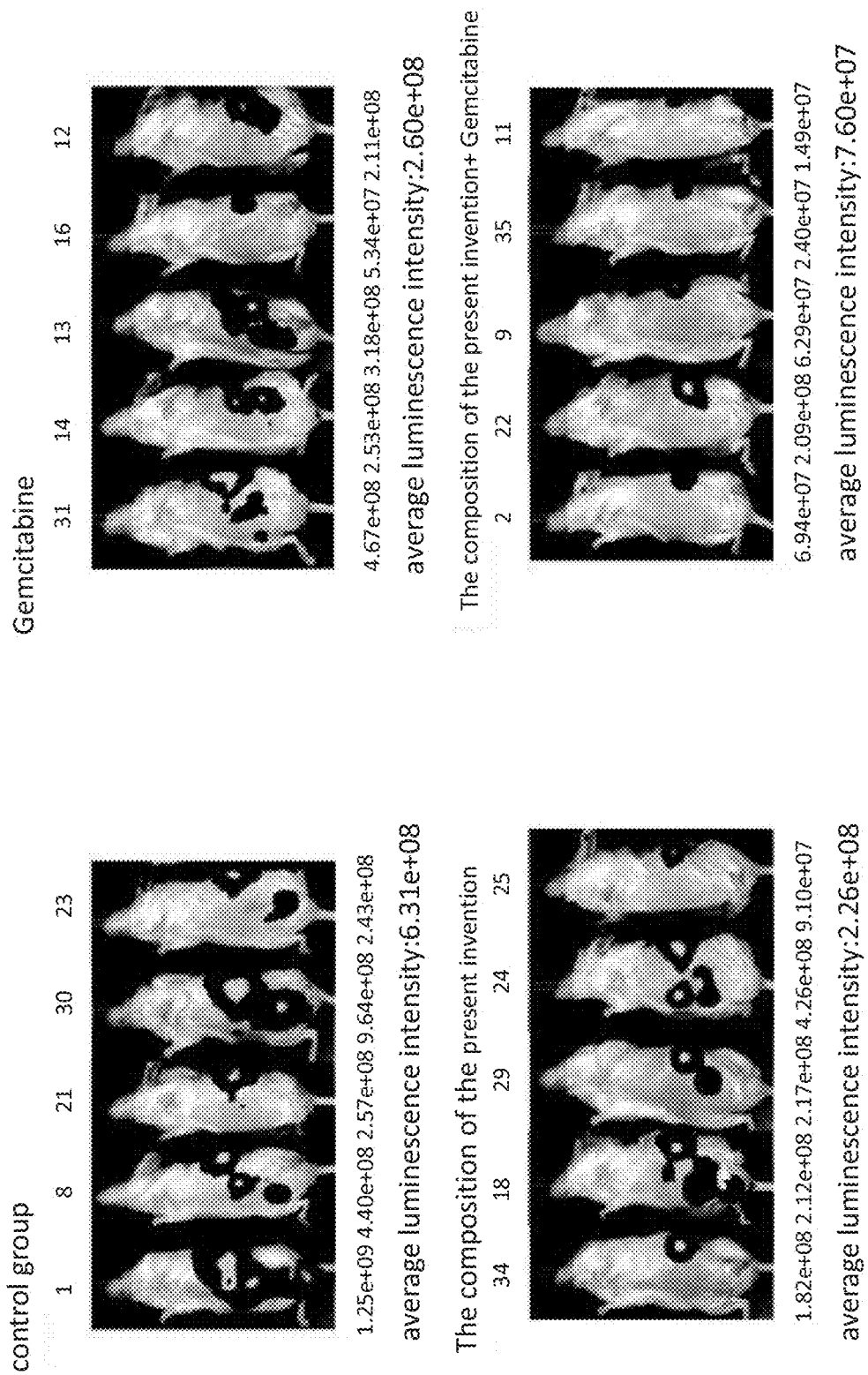
FIG. 15D is the bioluminescence image of the pancreatic cancer tumor with the treatment (II) of the composition of the present invention, gemcitabine, or the combination thereof on the 31$^{st}$ day of experiment.
Figure 15E:
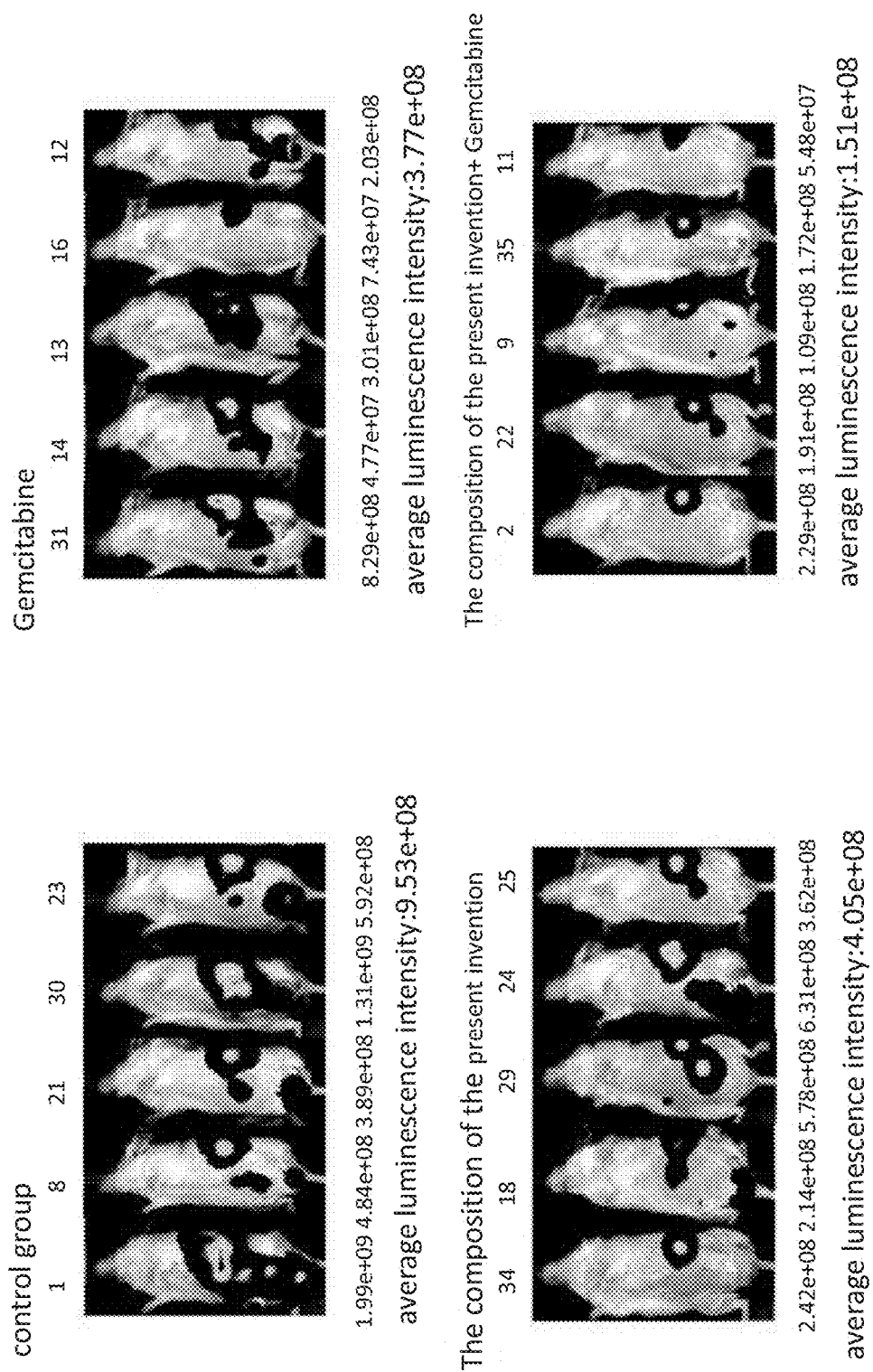
FIG. 15E is the bioluminescence image of the pancreatic cancer tumor with the treatment (II) of the composition of the present invention, gemcitabine, or the combination thereof on the 38$^{th}$ day of experiment.
Figure 15F:
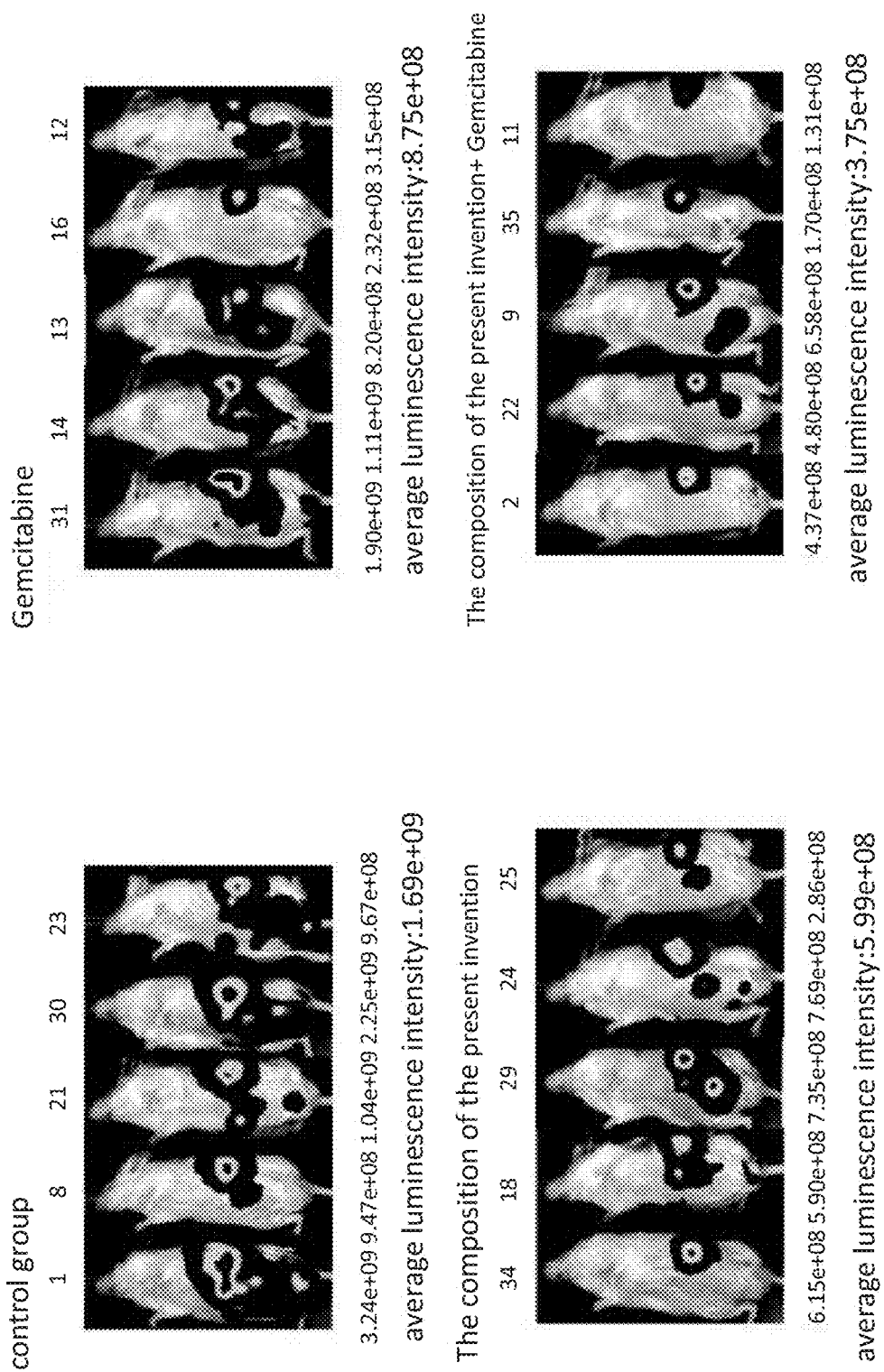
FIG. 15F is the bioluminescence image of the pancreatic cancer tumor with the treatment (II) of the composition of the present invention, gemcitabine, or the combination thereof on the 45$^{th}$ day of experiment.
Figure 15G:
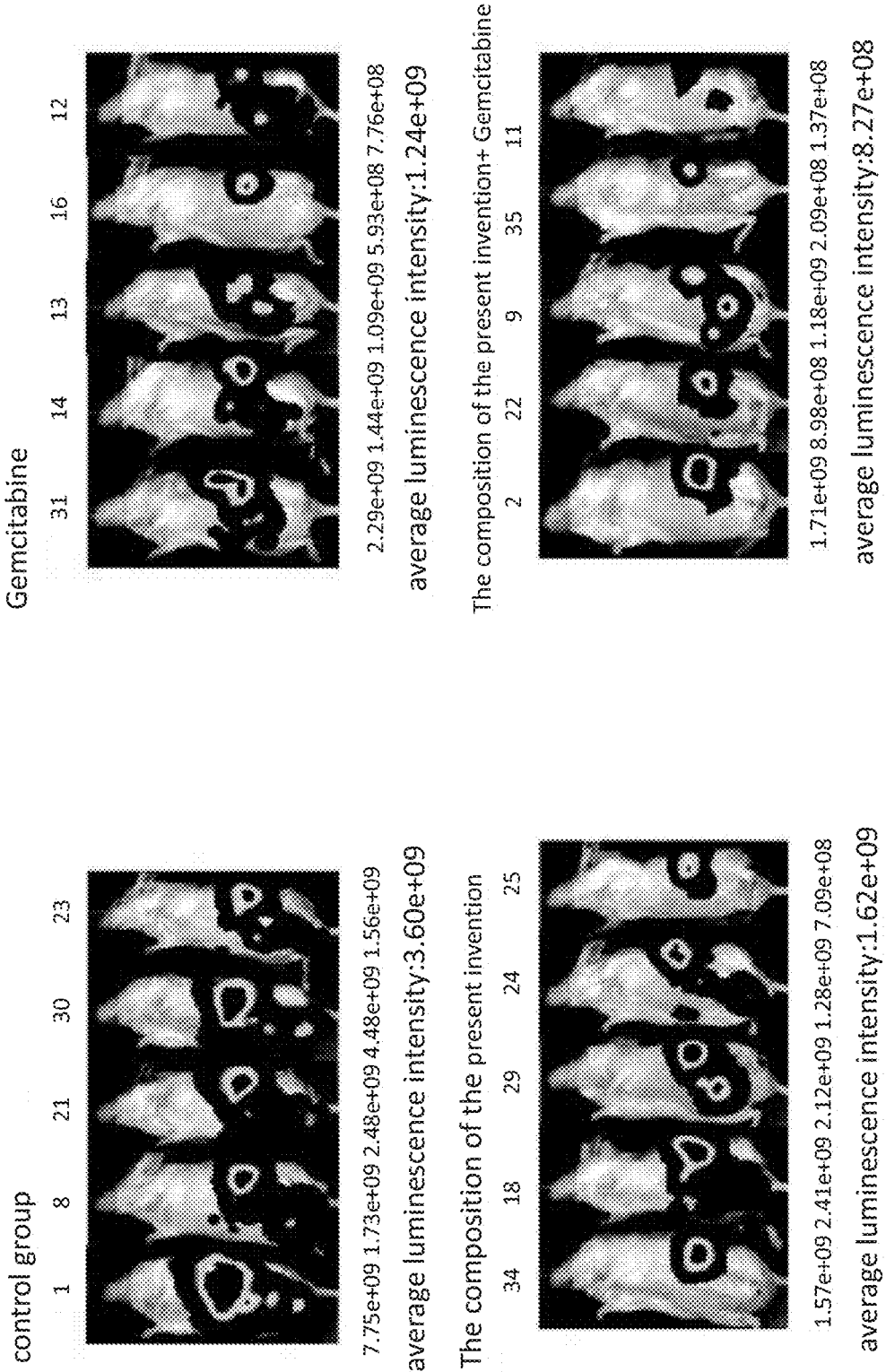
FIG. 15G is the bioluminescence image of the pancreatic cancer tumor with the treatment (II) of the composition of the present invention, gemcitabine, or the combination thereof on the 59$^{th}$ day of experiment.
Figure 16:
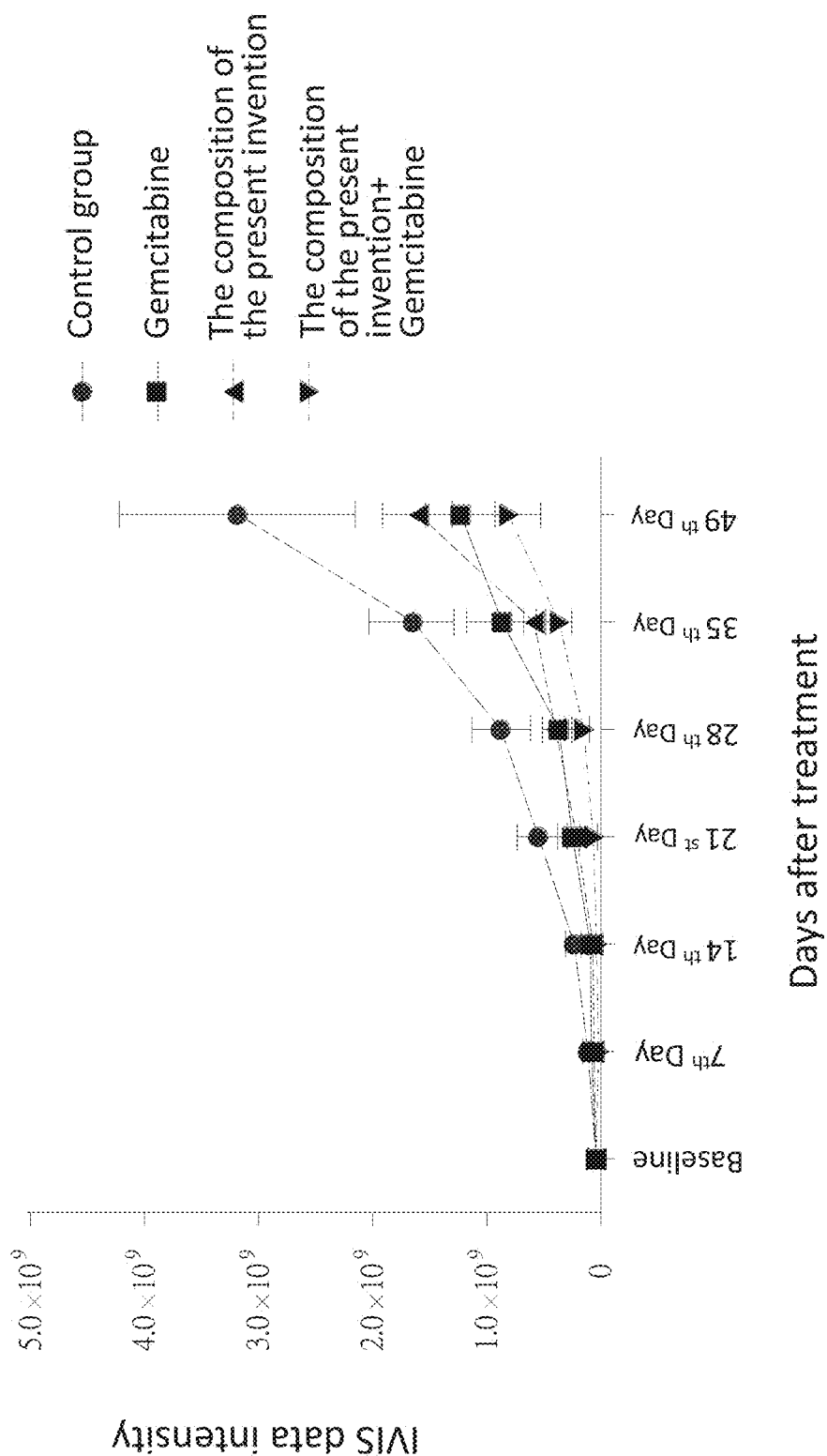
FIG. 16 is the run chart of the pancreatic cancer tumor development with the treatment (II) of the composition of the present invention, gemcitabine, or the combination thereof.

As shown in FIG. 12, jaundice was found in the mice of the gemcitabine group and the combination group, which meant that the emaciation, abnormal swollen gall, yellow dark skin, and abnormal yellow limbs and tail were observed in mice and also the malignant ascites occurred. Two groups of mice died one after another soon after jaundice was found. When it just occurred (9 weeks after treatment), the blood of all the mice in the experiment was collected, the T-bilirubin, GOT and GPT in the blood were examined, and the results thereof were shown in FIG. 13A to FIG. 13C. The T-bilirubin, GOT and GPT in the gemcitabine group and the combination group were significantly higher than those of the groups not treated with gemcitabine. Therefore, it can be deduced that continuously administering gemcitabine may cause sever jaundice. As shown in FIG. 14, among the 8 experimental mice in the control group, the first dead mouse was found on the $60^{th}$ day of the experiment, and the last dead mouse was found on the $91^{st}$ day of the experiment. The average survival period of the control group was 80.1 days. The jaundice was found in the experimental mice of the combination group and the gemcitabine group on the $9^{th}$ week after treatment and the massive death started to occur on the $10^{th}$ week after treatment (the $80^{th}$ day of the experiment). Regarding the gemcitabine group, the first dead mouse was found on the $77^{th}$ day of the experiment, while the last dead mouse was found on the $100^{th}$ day of the experiment, and the average survival period of the whole group was 89.4 days. Regarding the combination group, the first dead mouse was found on the $84^{th}$ day of the experiment, while the last dead mouse was found on the $108^{th}$ day of the experiment, and the average survival period of the whole group was 94.1 days. According to the aforementioned data of survival period, once the jaundice was found in the mice in these two groups, the mice would all die in around two weeks. Regarding the group of the composition of the present invention, the first dead mouse was found on the $88^{th}$ day of the experiment, while the last dead mouse was found on the $138^{th}$ day of the experiment, and the average survival period of the whole group was 106 days, which was 26 days more than that of the control group, showing the effect of extending the survival period of experimental mice of the orthotopic xenograft pancreatic cancer.

Example 7: The Therapeutic Effect (II) of Combination of Gemcitabine and the Composition of the Present Invention on the PDOX Pancreatic Cancer The human pancreatic adenocarcinoma cell line PANC-1 obtained from preparation example 2 was cloned and labelled with luminescence and fluorescence vector. The luminescence and fluorescence-labelled cells were implanted into pancreas of experimental mice (40 NOD-SCID experimental mice purchased from BioLASCO Taiwan Co., Ltd) with a cell number of $5 \times 10^5$ by surgery. 10 days after the cell implantation to the pancreas of the animals, the baseline data was measured by noninvasive in vivo imaging system (IVIS). After the baseline IVIS data were obtained, all the experimental mice were randomly and evenly assigned into groups [the value of mean±3 s.d. of measured IVIS data was calculated, and the animals having an IVIS data within the standard range were assigned into control group (physiological saline was used), the group of the composition of the present invention (24 mg/kg the composition obtained for preparation example 1 was administrated daily), gemcitabine group (100 mg/kg gemcitabine was administered by intravenous injection twice per week continuously for three weeks and discontinuing gemcitabine on the fourth week. These four weeks were named as gemcitabine cycle. There were three gemcitabine cycles in the present example.), and the combination group (100 mg/kg gemcitabine was administered by intravenous injection twice per week continuously for three weeks, and discontinuing gemcitabine on the fourth week, and the 24 mg/kg composition of the present invention obtained from the preparation example 1 were administered daily). The routes of administration were same as that of example 6; however, the dosage regimen were adjusted from example 6, because the jaundice was found in orthotopic xenograft pancreatic cancer mice after continuously administered with gemcitabine for 9 weeks in example 6 and died during the $10^{th}$ to $12^{th}$ weeks after treatment. The time points of IVIS data measurement of this example were: Baseline 10 Day (Baseline 10D), the $17^{th}$ day (7 days after treatment), the $24^{th}$ day (14 days after treatment), the $31^{st}$ day (21 days after treatment), the $38^{th}$ day (28 days after treatment), the $45^{th}$ day (35 days after treatment), and the $59^{th}$ day (49 days after treatment) of experiment. The blood of the experimental mice was collected and the T-bilirubin, GOT, and GPT in blood were examined to monitor the reason causing the jaundice on the fixed time points [Baseline 10 Day (Baseline 10D), the $4^{th}$ week after treatment, the $8^{th}$ week after treatment, the $10^{th}$ week after treatment, and the $12^{th}$ week after treatment,]. Whether the jaundice occurred or not was also observed by naked eyes. The jaundice signs of mice which could be observed by naked eyes included: emaciation, swollen gall, yellow dark skin, and abnormal yellow limbs and tail. The survival period of each mouse during the experiment was recorded.

As shown in FIG. 15A to FIG. 15G and FIG. 16, the group of the composition of the present invention also has excellent effect in inhibiting the tumor growth of the orthotopic xenograft pancreatic cancer compared to control group on the $49^{th}$ day after the treatment (with the inhibition effect of more than 50%). Said effect was similar to the effect shown in example 4 and example 6 on the 28th day after treatment. The trend of the tumor growth of the orthotopic xenograft pancreatic cancer also showed the same trend. Besides, the three examples, example 4, example 6 and example 7, consistently showed that the composition of the present invention had a therapeutic effect of more than 50% inhibition of the tumor growth of orthotopic xenograft pancreatic cancer. The trend of inhibition of the tumor growth of the orthotopic xenograft pancreatic cancer in the gemcitabine group was similar to the group of the composition of the present invention on the $49^{th}$ day after treatment, and their trends of tumor growth inhibition of IVIS data at the time points of the measurement during the 49 days of the experiment were also similar, with 50%-60% of the inhibition of the tumor growth of the orthotopic xenograft pancreatic cancer. Therefore, no significant difference was caused due to the change of the dosage regimen of the gemcitabine, because the therapeutic effect of 50%-60% in the inhibition of growth of the orthotopic xenograft pancreatic cancer was maintained from the $28^{th}$ day after the treatment to the $49^{th}$ day after the treatment. After the dosage regimen of gemcitabine was changed, the tumor growth inhibition effect of orthotopic xenograft pancreatic cancer in the combination group was better than the two single drug treatment groups (the group of the composition of the present invention and the gemcitabine group). The group of the composition of the present invention showed the effect of 80% or more in inhibiting tumor growth of the pancreatic cancer compared to control group, which was almost the same as that shown in example 6. The effects of inhibiting tumor growth of the combination group on the $28^{th}$ day and $49^{th}$ day after treatment (the effects of inhibiting tumor growth were 84% and 77% respectively) were not so different according to IVIS data thereof compared to that of the control group on the same time points of measurement. That is to say, the change of the dosage regimen did not affect therapeutic effect on the advanced stage in the combination group. Therefore, the animal experiment repeated in this example ensures that the combination of the composition of the present invention and the gemcitabine, the clinical first-line drug of pancreatic cancer, has the better effect in inhibiting the tumor growth of the orthotopic xenograft pancreatic cancer.

Figure 17A:
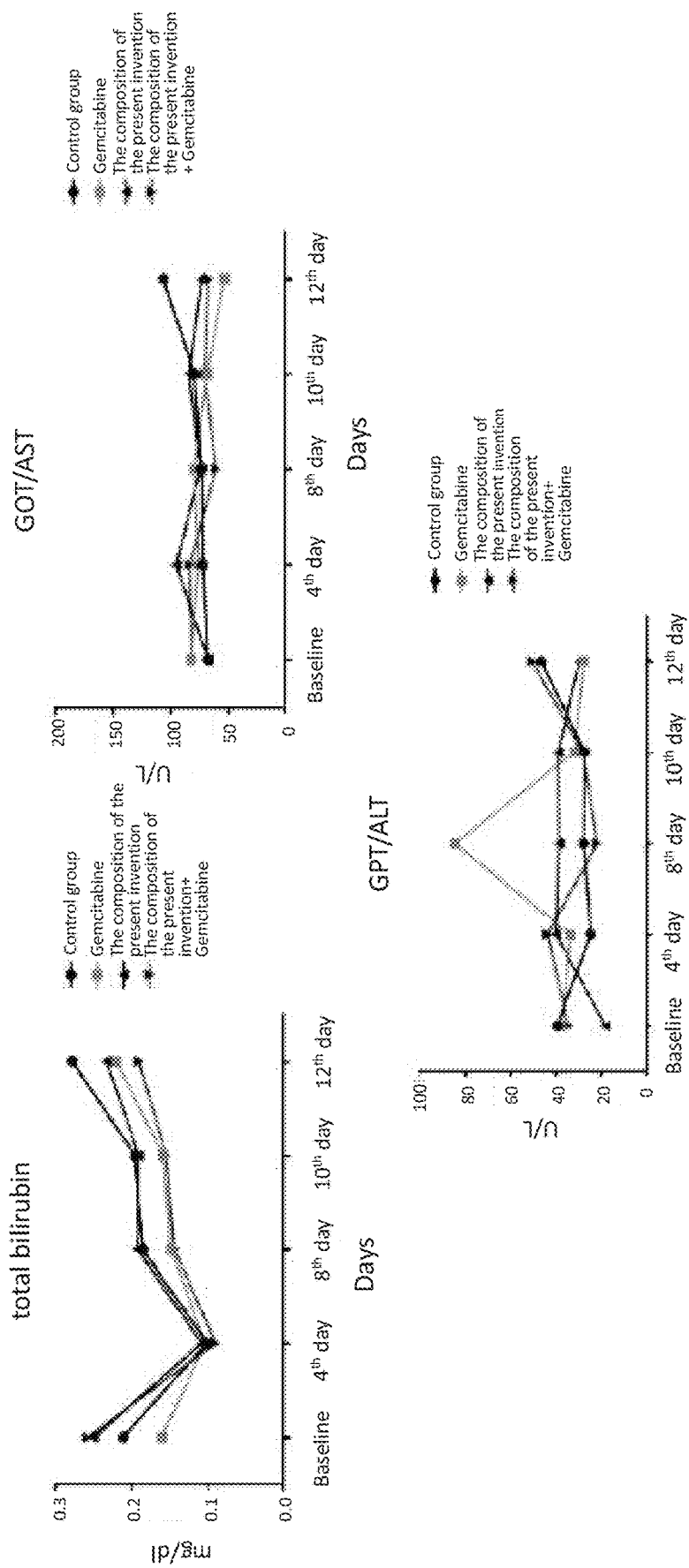
FIG. 17A is the average run charts showing total bilirubin, GOT/AST, and GPT/ALT in blood samples of each group of the experimental animals with the treatment (II) of: the composition of the present invention, gemcitabine, or the combination thereof for the pancreatic cancer tumor.
Figure 17B:
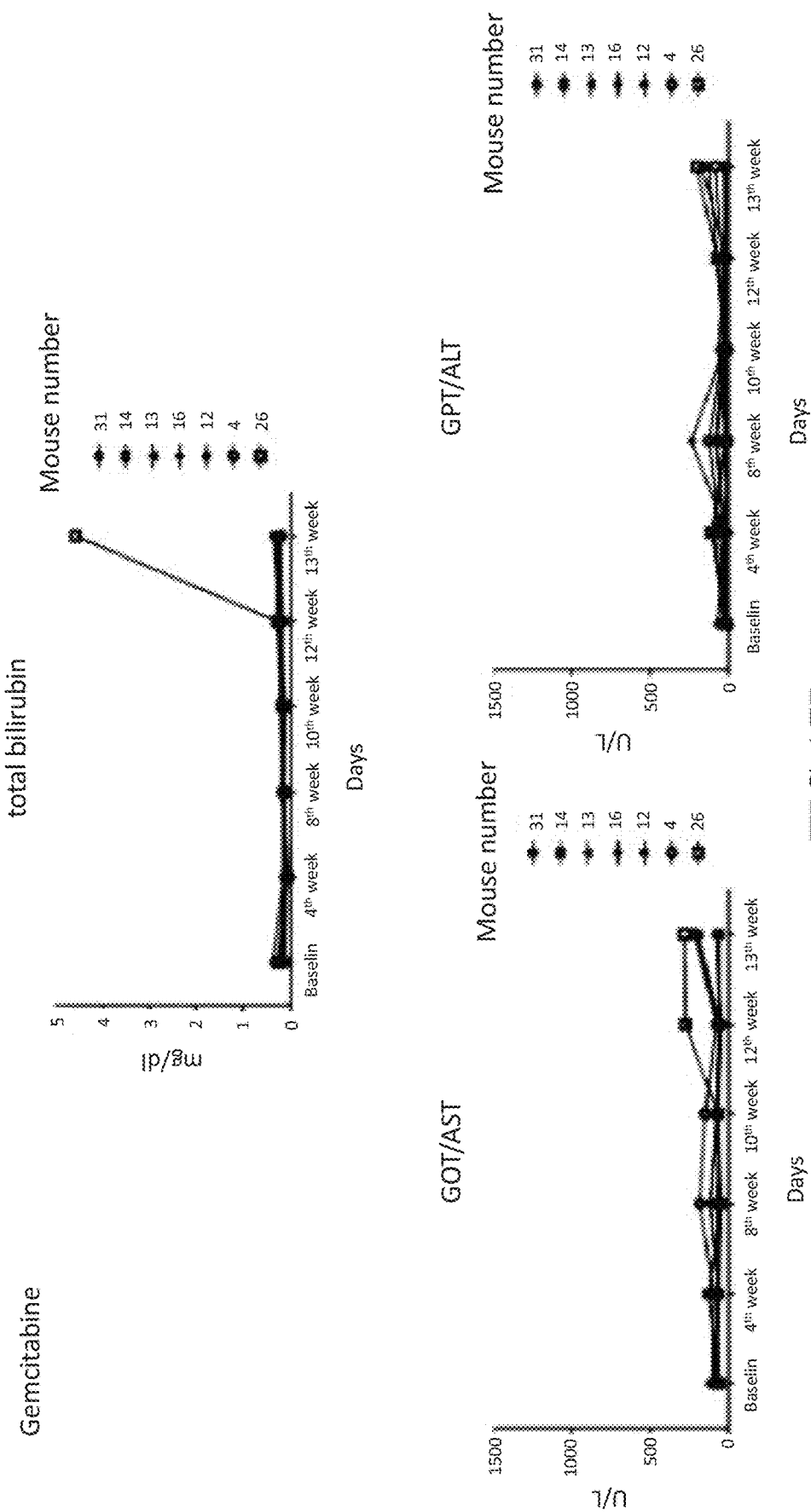
FIG. 17B is the run charts showing total bilirubin, GOT/AST, and GPT/ALT in blood samples of each group of the experimental animals with the treatment (II) of gemcitabine for the pancreatic cancer tumor.
Figure 17C:
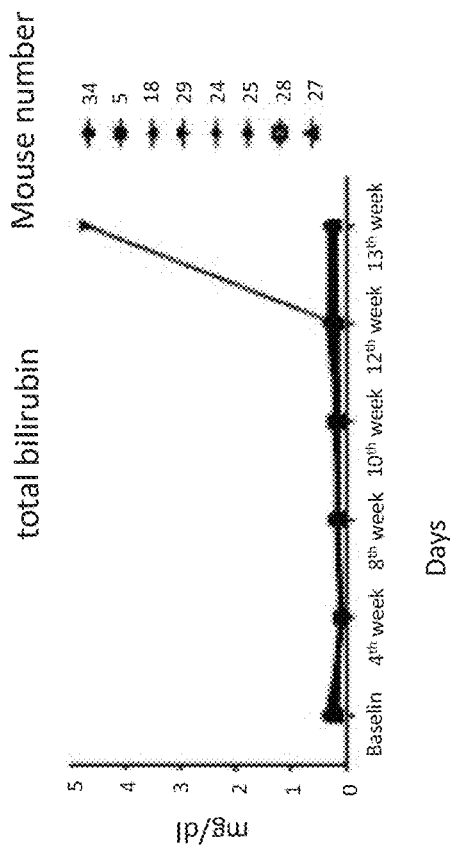
FIG. 17C is the run charts showing total bilirubin, GOT/AST, and GPT/ALT in blood samples of each group of the experimental animals with the treatment (II) of the composition of the present invention for the pancreatic cancer tumor.
Figure 17C:
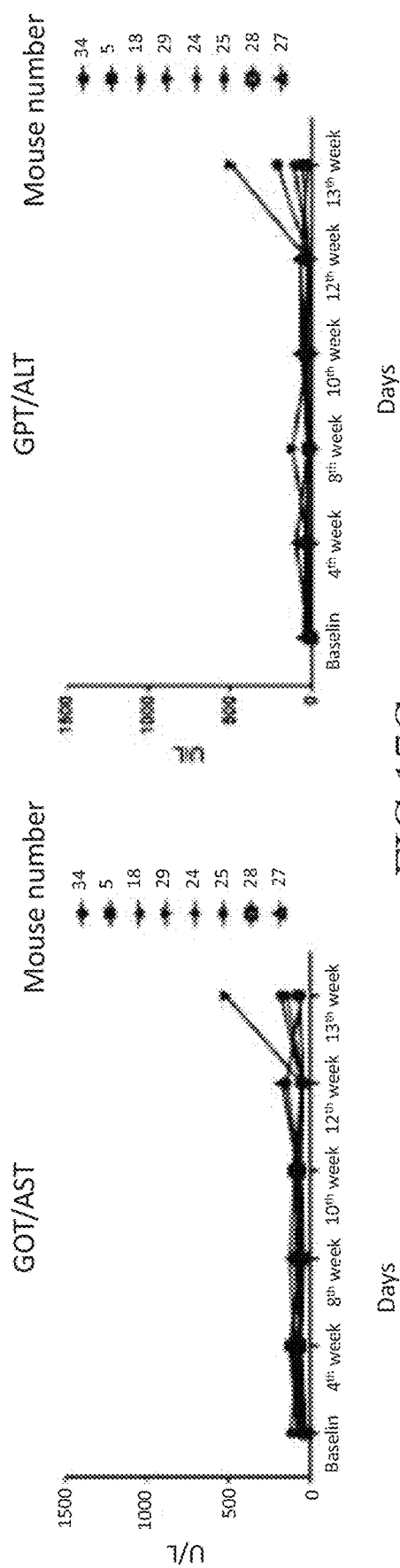
Figure 17D:
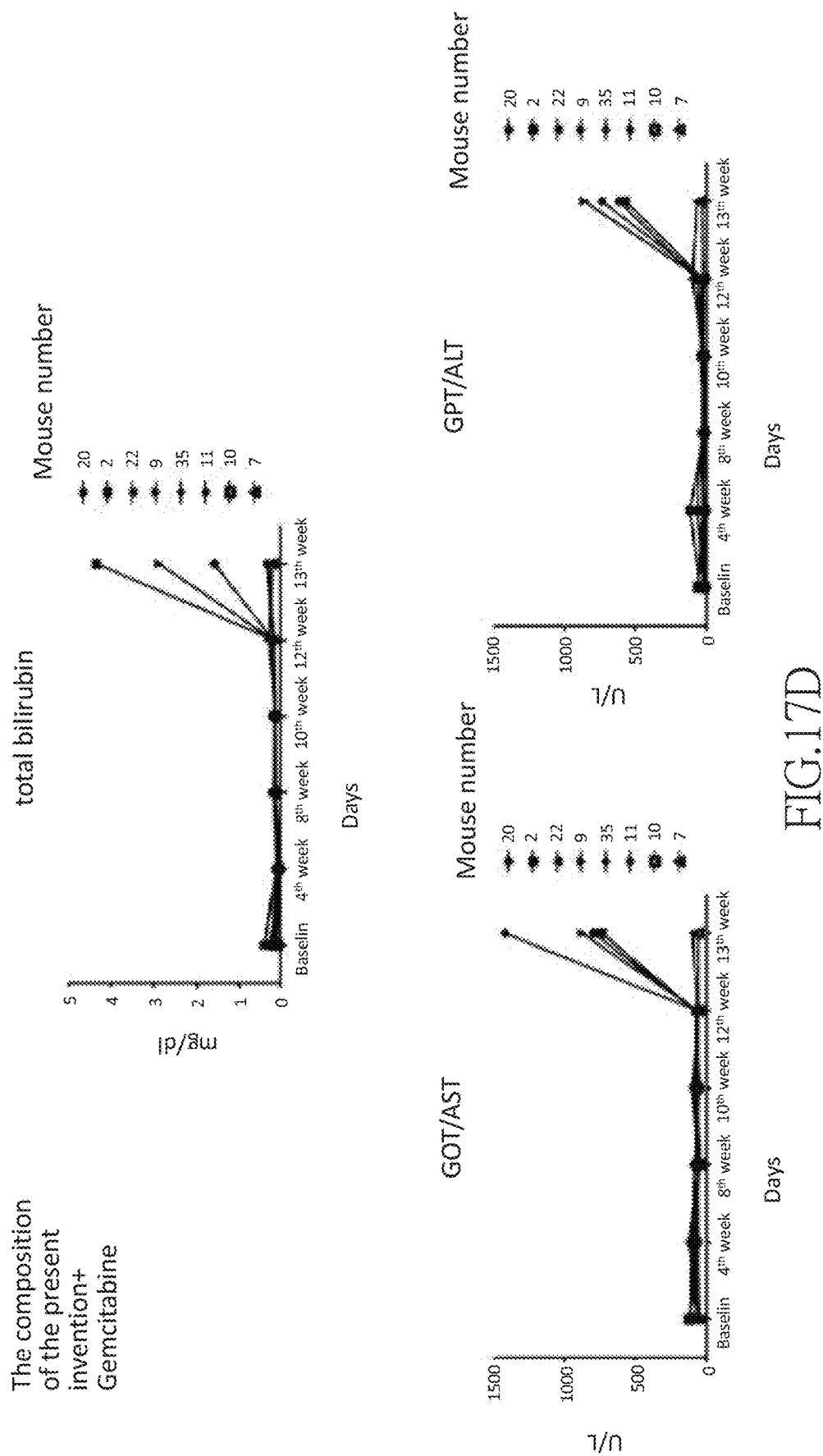
FIG. 17D is the run charts showing total bilirubin, GOT/AST, and GPT/ALT in blood samples of each group of the experimental animals with the treatment (II) of the combination of composition of the present invention and gemcitabine for the pancreatic cancer tumor.
Figure 18:
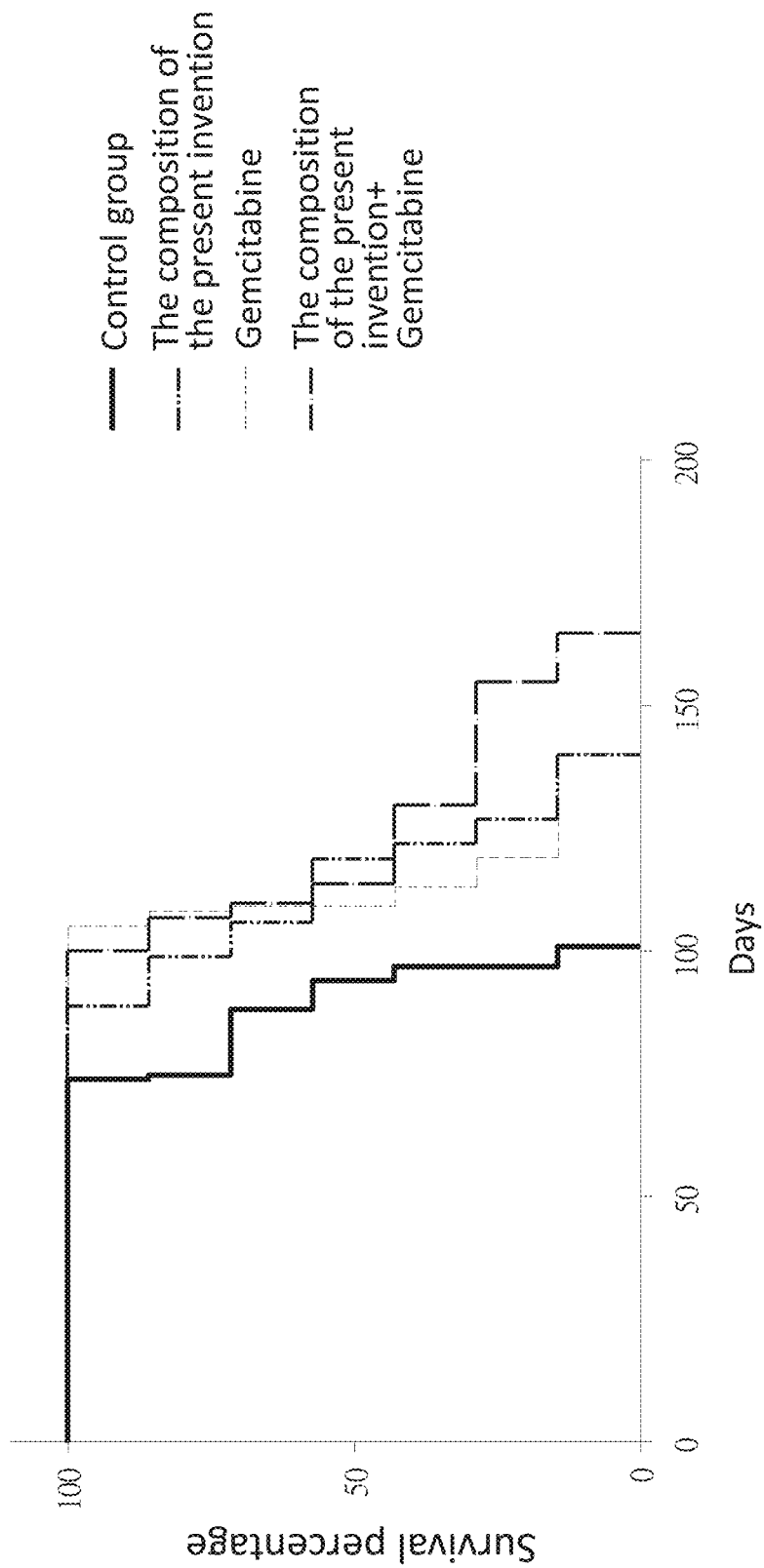
FIG. 18 is the survival chart of the experimental mice with the treatment (II) of: the composition of the present invention, gemcitabine, or the combination thereof for the pancreatic cancer tumor.

FIG. 17A to FIG. 17D show the monitoring results of T-bilirubin, GOT and GPT after the blood collection at the fixed time points. There were totally five time points: Baseline 10 Day, the $4^{th}$ week after treatment, the $8^{th}$ week after treatment (the $4^{th}$ week after treatment and the $8^{th}$ week after treatment were the same time points of the end of the first gemcitabine cycle and second gemcitabine cycle, respectively), the $10^{th}$ week after treatment and the $12^{th}$ week after the treatment (the $10^{th}$ week after treatment and the $12^{th}$ week after treatment were the same time points of the beginning and the end of the third gemcitabine cycle, respectively). The time point of blood collection on the $13^{th}$ week after treatment was an extra time point of blood collection for monitoring, because the mice were found abnormal and the jaundice occurred. As shown in FIG. 17A, the three monitoring items using the collected blood in the first 12 weeks after treatment were all in the blood biochemistry reference range (the reference range: T-bilirubin: 0-1 mg/dl, GOT/AST: 40-100 U/L; GPT/ALT: 30-50 U/L). The GPT value of gemcitabine group was abnormally raised on the $8^{th}$ week after treatment, which might result from hemolysis or machine error of the sample from one experimental mouse in the group, and the GPT value was back to normal on the $10^{th}$ week after treatment. The values of T-bilirubin and GOT of the control group were slightly higher compared to the other three experimental groups on the $10^{th}$ week after treatment. However, the mice of the control group started to die from the $10^{th}$ week after treatment, so the average values of three items in blood test were not that significantly different from other groups. On the $13^{th}$ week after treatment (one week after the end of the third gemcitabine cycle), except the control group (only one experimental mouse was left), there were 1 to 2 experimental mice showing the symptom of jaundice such as emaciation, abnormal swollen gall, yellow dark skin, and abnormal yellow limbs and tail in the three experimental groups (the group of the composition of the present invention, the gemcitabine group, and the combination group). Therefore, the blood collection and examination were conducted immediately. The trend results of T-bilirubin, GOT and GPT were shown in FIG. 17B, FIG. 17C, and FIG. 17D. Regarding the T-bilirubin observed from the three figures, one mouse in each of the group of the composition of the present invention and the gemcitabine group had the value higher than the standard, and three experimental mice in the combination group had the value higher than the standard (0.1-0.9 mg/mL). The experimental mice having T-bilirubin higher than the standard started to die in ten days. After blood collection conducted on the $13^{th}$ week in the gemcitabine group, the jaundice was found in the experimental mice, which was not found at the beginning, and the mice with jaundice died soon after the jaundice was found. The survival period of the experimental mice of this example was shown in FIG. 18 and the following Table 4.

TABLE 4

The survival period of the mice in the control group and the experimental groups

| Groups | Control group | The composition of the present invention | gemcitabine group | Combination group |
|---|---|---|---|---|
| Survival period of the experimental mice (Days) | 74 | 89 | 105 | 100 |
| | 75 | 99 | 108 | 107 |
| | 88 | 106 | 109 | 110 |
| | 94 | 119 | 109 | 114 |
| | 97 | 122 | 113 | 130 |
| | 97 | 127 | 119 | 155 |
| | 101 | 140 | 140 | 165 |
| Average survival period (Days) | 89.4 | 114.6 | 114.7 | 126 |

It could be seen that, the survival period of the group of the composition of the present invention was longer than that of the control group, and this was consistent with the results shown in example 4 and example 6. The longest survival period of the experimental mouse of the group of the composition of the present invention was 140 days, and its average survival period was around 25.2 days longer than that of the control group. Therefore, the composition of the present invention can extend the survival period of the experimental mice of the orthotopic xenograft pancreatic cancer. Besides, the dosage regimen of the gemcitabine was different from that used in example 6, and the experimental mice treated with the gemcitabine, including the gemcitabine group and the combination group, showed longer survival period than the mice of corresponding groups of example 6. Once the jaundice was found in the experimental mice, they would start to die in a short time (the 13$^{th}$ week after treatment and the 14$^{th}$ week after treatment). However, if the experimental mice can survive this period of time, they would have longer survival period. Besides, the longest survival period of the mouse in the combination group was more than 150 days, which was about 36 days longer than that of the control group. The survival period of the mice treated with the combination group was longer than that of the composition of the present invention and the gemcitabine group. Only data from 7 mice in each group was shown in the table because one mouse from each group was used for dissection.

Example 8: The Effect of the Composition of the Present Invention on the Pancreatitis Three dogs with a too high value of the blood amylase, the indication of the pancreatitis (with a normal value of 500-1500 U/L), were continuously administered with the composition of the present invention once per day with a dosage of 10 mg/10 kg/day by tube feeding for one week, and then the amylase was examined. One dog with the normal amylase value was used as control group, which was only administered with physiological saline as supportive treatment. The amylase value in the blood of experimental animals of each group were traced to determine whether the pancreatitis ameliorated or not. As the results shown in the following Table 5, the abnormal amylase in the blood of the dogs treated with the composition of the present invention decreased, compared to the control group administered with physiological saline. Therefore, the composition of the present invention has the effect of ameliorating the pancreatitis. Although not recorded in the table, the pancreatitis of cats was also ameliorated after administering the composition of the present invention, which meant that the value of amylase, an indication of pancreatitis, went down to the normal value.

TABLE 5

The effect on the dogs with pancreatitis treated with the composition of the present invention for one week

| | Amylase (U/L) |
|---|---|
| Dog A | 1758 |
| | 745 |
| Dog B | 2029 |
| | 1771 |
| Dog C | 1825 |
| | 1141 |
| Dog of control group | 1579 |
| | 1929 |

To sum up, the composition comprising ferrous amino acid particles (the composition of the present invention) can treat or ameliorate the pancreas-related disease. Specifically, the composition of the present invention could inhibit the growth of the pancreatic cancer cells, induce cell death of the pancreatic cancer cells, inhibit the migration ability and invasion ability of the pancreatic cancer cells, inhibit the tumor growth of orthotopic xenograft pancreatic cancer, ameliorate the spread of orthotopic xenograft pancreatic cancer, ameliorate or decrease the malignant ascites from the advanced orthotopic xenograft pancreatic cancer, cause less side effect of hepatotoxicity, and show better effect of inhibiting the growth of the pancreatic tumor when it is administered with gemcitabine, the first-line drug of the pancreatic cancer. Besides, the composition of the present invention can treat or ameliorate the pancreatitis.

It is obvious to a person having ordinary skill in the art that any amendment and modification according to the present invention are not departing from the scope and the spirit of the present invention. Although the preferred embodiments are disclosed in the present invention, it should be understood that the present invention should not be unduly limited to the specific embodiments. In fact, any simple modifications and changes of the above embodiments of the present invention, which are obvious to the person having ordinary skill in the art, are encompassed in the claims.

What is claimed is:

1. A method for treating or ameliorating a pancreas-related disease, comprising administering to a subject in need thereof a medicament comprising an effective amount of a composition and a pharmaceutically acceptable carrier, wherein the composition comprises ferrous amino acid chelate particles sintered from ferrous amino acid chelate, the ferrous amino acid chelate is ferrous glycinate chelate, the average particle size of the ferrous amino acid chelate particles ranges from 500 nm to 2600 nm, and the average molecular weight of the ferrous amino acid chelate particles ranges from 1,500 Dalton to 600,000 Dalton,
wherein the pancreas-related disease is selected from the group consisting of pancreatic cancer, pancreatic cancer metastasis, ascites produced from pancreatic cancer, and pancreatitis.

2. The method according to claim 1, wherein the composition is administrated to a human.

3. The method according to claim 1, wherein the effective amount ranges from 0.1 mg/kg/day to 120 mg/kg/day.

4. The method according to claim 1, wherein the composition is administered with gemcitabine.

5. The method according to claim 4, wherein the gemcitabine is administered with a dosage regimen comprising one or more gemcitabine cycles, and each gemcitabine cycle is composed of administering gemcitabine twice per week for three weeks and discontinuing gemcitabine on the fourth week.

* * * * *